US012653621B2

(12) United States Patent
Gehriger et al.

(10) Patent No.: US 12,653,621 B2
(45) Date of Patent: Jun. 16, 2026

(54) BONE LANDMARKS EXTRACTION BY BONE SURFACE PALPATION USING BALL TIP STYLUS FOR COMPUTER ASSISTED SURGERY NAVIGATION

(71) Applicant: GLOBUS MEDICAL, INC., Audubon, PA (US)

(72) Inventors: Daniel Gehriger, Lausanne (CH); Szymon Kostrzewski, Lausanne (CH); Benoit Brot, Lausanne (CH); Hayden Cameron, Philadelphia, PA (US); Marc-Henri Primault, Saint-George (CH); Olivier Chappuis, Lutry (CH)

( * ) Notice: Subject to any disclaimer, the term of this patent is extended or adjusted under 35 U.S.C. 154(b) by 772 days.

(21) Appl. No.: 18/057,996

(22) Filed: Nov. 22, 2022

(65) Prior Publication Data

US 2024/0164844 A1     May 23, 2024

(51) Int. Cl.
*A61B 34/20* (2016.01)
*A61F 2/46* (2006.01)
*A61B 90/00* (2016.01)

(52) U.S. Cl.
CPC .............. *A61B 34/20* (2016.02); *A61F 2/461* (2013.01); *A61B 2034/2072* (2016.02); *A61B 2090/363* (2016.02)

(58) Field of Classification Search
CPC ............ A61B 34/20; A61B 2034/2055; A61B 2034/2068; A61B 2034/2072; A61B 2090/363; A61B 2090/3983; A61F 2/461
See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |

(Continued)

FOREIGN PATENT DOCUMENTS

| | | | |
|---|---|---|---|
| EP | 3936079 A1 * | 1/2022 | ............. A61B 90/39 |
| WO | 2021263174 A1 | 12/2021 | |

OTHER PUBLICATIONS

US 8,231,638 B2, 07/2012, Swarup et al. (withdrawn)

*Primary Examiner* — Anu Ramana

(57) ABSTRACT

A system for computer assisted navigation during surgery. At least one processor operates to identify locations of fiducials of a reference element on a ball tip stylus in images obtained from tracking cameras with at least partially overlapping field-of-views imaging the ball tip stylus with a ball palpating a surface of a bone. Operations determine locations of a center of the ball based on the locations of the fiducials of the reference element, and define an offset-acquired surface of the bone based on mathematically connecting the locations of the center of the ball. Operations determine local normal vectors to the offset-acquired surface for the locations of the center of the ball. Operations translate the offset-acquired surface of the bone toward the surface of the bone along the local normal vectors based on a radius of the ball to define an acquired surface of the bone.

19 Claims, 18 Drawing Sheets

(56) References Cited

U.S. PATENT DOCUMENTS

| | | | |
|---|---|---|---|
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,827,723 B2 | 12/2004 | Carson |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,923,817 B2 | 8/2005 | Carson et al. |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,715,602 B2 | 5/2010 | Richard |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |

(56)                References Cited

U.S. PATENT DOCUMENTS

| | | |
|---|---|---|
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Arkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,165,659 B2 * | 4/2012 | Sheffer ............... A61B 34/20 |
| | | 600/407 |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |

(56) References Cited

U.S. PATENT DOCUMENTS

| | | |
|---|---|---|
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,568,416 B2 * | 10/2013 | Schmitz ......... A61B 17/320016 606/79 |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,532,845 B1 * | 1/2017 | Dossett ................. A61B 34/10 |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 12/2017 | Donner et al. |
| 9,848,922 B2 | 12/2017 | Tohmeh et al. |
| 9,901,463 B2 | 2/2018 | Mahfouz |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,398,514 B2 | 9/2019 | Ryan et al. |
| 10,499,996 B2 | 12/2019 | de Almeida Barreto |
| 10,517,681 B2 * | 12/2019 | Roh ...................... A61B 34/20 |
| 10,687,856 B2 | 6/2020 | Park et al. |
| 10,952,753 B2 | 3/2021 | McAuliffe et al. |
| 11,026,700 B2 | 6/2021 | Shah |
| 11,045,227 B2 | 6/2021 | Park et al. |
| 11,045,330 B2 | 6/2021 | Mahfouz |
| 11,234,770 B2 * | 2/2022 | Berend ................. A61B 34/20 |
| 11,331,070 B2 * | 5/2022 | Erkamp .............. A61B 8/0841 |
| 2001/0036302 A1 | 11/2001 | Miller |
| 2002/0035321 A1 | 3/2002 | Bucholz et al. |
| 2002/0147415 A1 | 10/2002 | Martelli |
| 2004/0068172 A1 | 4/2004 | Nowinski et al. |

(56)                    References Cited

U.S. PATENT DOCUMENTS

| | | |
|---|---|---|
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0208081 A1 | 8/2008 | Murphy et al. |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |

(56)  References Cited

U.S. PATENT DOCUMENTS

| | | |
|---|---|---|
| 2014/0073914 A1 | 3/2014 | Avallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0049622 A1 | 2/2018 | Ryan et al. |
| 2019/0369752 A1 | 12/2019 | Keda et al. |
| 2020/0197113 A1 | 6/2020 | Felenc |
| 2021/0338149 A1 | 11/2021 | Angelo |

* cited by examiner

810 OFFSET-ACQUIRED SURFACE

500 BALL TIP STYLUS

804 NORMAL TO THE PLANE

800 CENTER OF THE BALL TIP

802 RADIUS

820 BONE

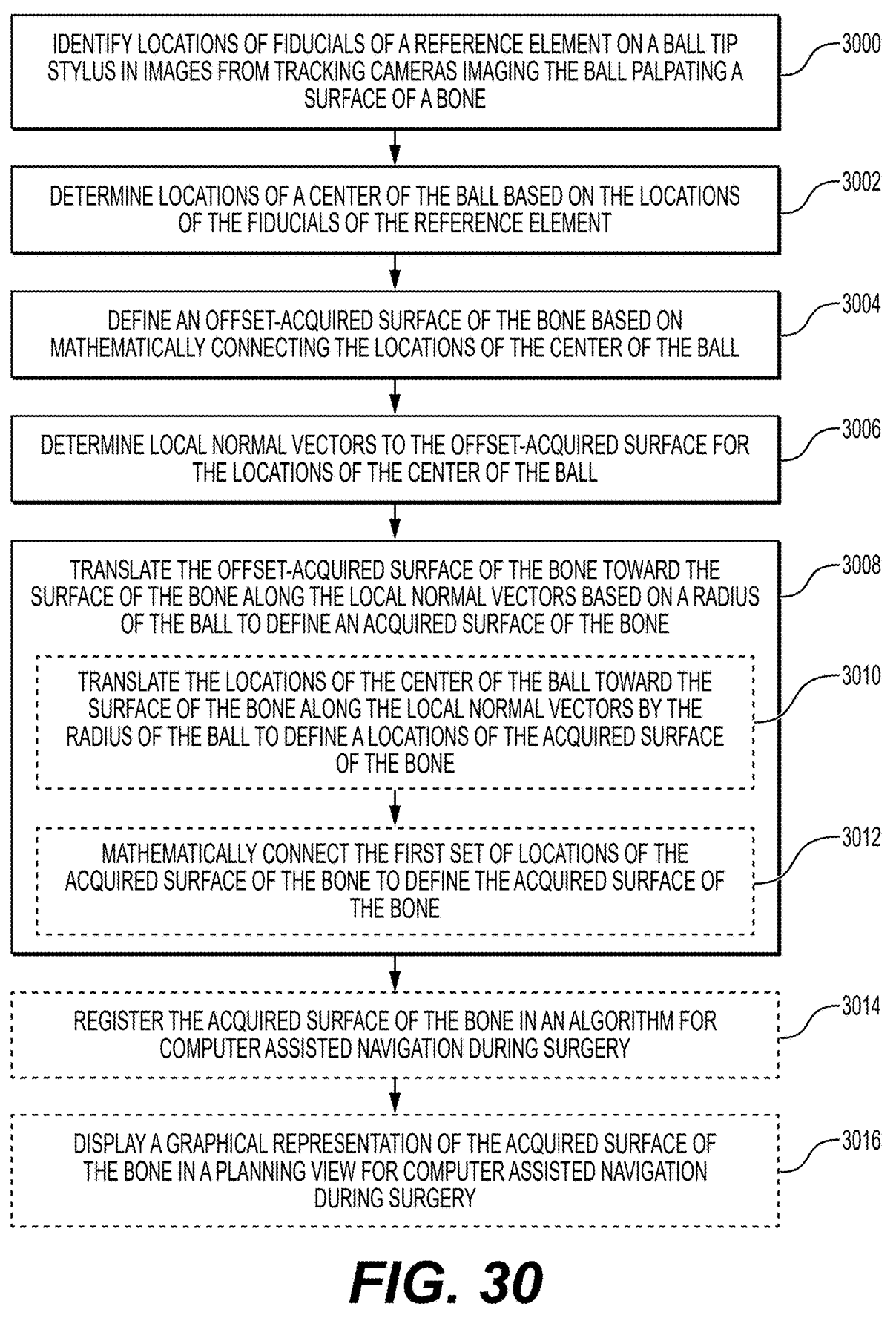

IDENTIFY LOCATIONS OF FIDUCIALS OF A REFERENCE ELEMENT ON A BALL TIP STYLUS IN IMAGES FROM TRACKING CAMERAS IMAGING THE BALL PALPATING A SURFACE OF A BONE ⟶ 3000

DETERMINE LOCATIONS OF A CENTER OF THE BALL BASED ON THE LOCATIONS OF THE FIDUCIALS OF THE REFERENCE ELEMENT ⟶ 3002

DEFINE AN OFFSET-ACQUIRED SURFACE OF THE BONE BASED ON MATHEMATICALLY CONNECTING THE LOCATIONS OF THE CENTER OF THE BALL ⟶ 3004

DETERMINE LOCAL NORMAL VECTORS TO THE OFFSET-ACQUIRED SURFACE FOR THE LOCATIONS OF THE CENTER OF THE BALL ⟶ 3006

TRANSLATE THE OFFSET-ACQUIRED SURFACE OF THE BONE TOWARD THE SURFACE OF THE BONE ALONG THE LOCAL NORMAL VECTORS BASED ON A RADIUS OF THE BALL TO DEFINE AN ACQUIRED SURFACE OF THE BONE ⟶ 3008

TRANSLATE THE LOCATIONS OF THE CENTER OF THE BALL TOWARD THE SURFACE OF THE BONE ALONG THE LOCAL NORMAL VECTORS BY THE RADIUS OF THE BALL TO DEFINE A LOCATIONS OF THE ACQUIRED SURFACE OF THE BONE ⟶ 3010

MATHEMATICALLY CONNECT THE FIRST SET OF LOCATIONS OF THE ACQUIRED SURFACE OF THE BONE TO DEFINE THE ACQUIRED SURFACE OF THE BONE ⟶ 3012

REGISTER THE ACQUIRED SURFACE OF THE BONE IN AN ALGORITHM FOR COMPUTER ASSISTED NAVIGATION DURING SURGERY ⟶ 3014

DISPLAY A GRAPHICAL REPRESENTATION OF THE ACQUIRED SURFACE OF THE BONE IN A PLANNING VIEW FOR COMPUTER ASSISTED NAVIGATION DURING SURGERY ⟶ 3016

*FIG. 30*

BONE LANDMARKS EXTRACTION BY BONE SURFACE PALPATION USING BALL TIP STYLUS FOR COMPUTER ASSISTED SURGERY NAVIGATION

FIELD

The present disclosure relates to medical devices and systems, and more particularly, bone surface determination for computer assisted navigation during surgery.

BACKGROUND

Computer assisted surgery navigation systems have become a well-established technique in operating rooms for providing surgeons with computerized visualization of how a surgical instrument or other device that is posed relative to a patient correlates to a pose relative to medical images of the patient's anatomy, and how those poses correlate to a pre-operative surgical plan. Camera tracking systems for computer assisted surgery navigation typically use a set of tracking cameras to track pose of a reference element on the surgical instrument, which is being positioned by a surgeon during surgery, relative to a patient reference element (also "dynamic reference base" (DRB)) affixed to a patient. A computer model of a real instrument is associated with a reference element, so that the computer model can be overlaid on registered images of patient's anatomy. The camera tracking system uses the relative poses of the reference elements to determine how the real instrument is posed relative to a patient and to determine how the computer model of the real instrument is to be correspondingly posed as on overlay on the medical images. The surgeon can thereby use real-time visual feedback of the relative poses to navigate the surgical instrument during a surgical procedure on the patient.

There are a number of surgical interventions requiring osteotomy, i.e. cutting an anatomical structure such as a bone along a target plane. Total knee arthroplasty typically requires cutting both the femoral epiphysis and tibial epiphysis in order to remove the damaged bone and cartilage and prepare the bones for installation of a knee prosthesis.

A robotic system can be used which has a serial arm on which a passive structure guiding the saw blade is mounted. For example, a sagittal saw can be attached to the end of the passive structure to guide the cutting plane. The system can enable a surgeon to hold the sagittal saw and cut bones while watching on the navigation system (e.g., stand-alone displays or Augmented Reality (AR) headset) various types of relevant feedback and information associated with a defined plan for and/or progress of the surgical procedure.

The serial arm can moved through computer guided control to a suitable position for the surgery, e.g., pursuant to the surgeon's request which may be provided via a foot pedal, touchscreen, AR interaction, etc. The passive structure allows the surgeon to precisely remove bone in the cutting plane. Bone removal progression can be measured through camera tracking of fiducials (e.g., optical tracking markers in the form of a disk or sphere) of a reference element attached to the bones and to the sagittal saw.

Various workflows can be available for use with the system. Some workflows require preoperative scans or images of the patient (e.g., x-ray, Computerized Tomography (CT)). On the other hand, an imageless workflow does not require any pre-operative images. To obtain intra-operative information about the patient anatomy, the surgeon measures key parameters of the bone using a camera tracking system and appropriate tracked instrument to capture points on patient anatomy. Later, this information is used to plan the implant position and orientation with respect to patient anatomy and navigate the robot and surgical instruments during bone resection and implant placement.

Some workflows include having the surgeon rigidly attach a reference element to each bone, where the reference element includes fiducials which are detected by tracking cameras for computer assisted navigation (e.g., infrared or visible light cameras). The reference elements allow tracking of bone position by the navigation system. The reference elements can be positioned on the bone in the following way: attached with fixation structures (e.g., screw pins, "crocodile" jaws) on the bones (tibia and femur) and oriented so as they can be seen by the tracking cameras of the navigation system. The reference elements positions and orientations must stay rigidly fixed with respect to the bone.

Another step of various workflows is to register the patient in tracking space of the navigation system. Patient registration can include matching the patient anatomy (e.g., tibia and femur in the context of total knee arthroplasty) with numeric representation of the corresponding bone, usually a 3D model of the bone. The bone representation may be either constructed from a set of CT images (CT workflow) or based on a generic bone model (Imageless workflow).

In an optional step, the rough position of the bone in reference to the bone-attached reference element is identified. The step can include having the surgeon measure natural landmarks (such as Whiteside's line, transepicondylar line, malleolus sides, etc.) by acquiring their localization on the bones, or acquiring specific points that are further used to calculate axes.

Additionally, the surgeon can move the leg in front of the tracking cameras through a pre-defined set of moves, in order to determine other natural landmarks (such as hip center of rotation or joint planes) to perform operations for acquired trajectory of Reference Elements and further calculation.

Although current surgical procedures offer sophisticated computer assisted navigation once bone landmarks of a patient has been properly registered for tracking, current procedures for registration should be improved to be more automated and result in more accurate tracking during surgery.

SUMMARY

Some embodiments of the present disclosure are directed to a system for computer assisted navigation during surgery. The system includes at least one processor that operates to identify locations of fiducials of a reference element on a ball tip stylus in images obtained from tracking cameras with at least partially overlapping field-of-views imaging the ball tip stylus with a ball painting/palpating a surface of a bone. Operations determine locations of a center of the ball based on the locations of the fiducials of the reference element. Operations define an offset-acquired surface of the bone based on mathematically connecting the locations of the center of the ball. Operations determine local normal vectors to the offset-acquired surface for the locations of the center of the ball. Operations translate the offset-acquired surface of the bone toward the surface of the bone along the local normal vectors based on a radius of the ball to define an acquired surface of the bone.

In some further embodiments, the operation to translate the offset-acquired surface of the bone to define the acquired surface of the bone, includes to translate the first set of locations of the center of the ball toward the surface of the bone along the first set of local normal vectors by the radius of the ball to define a first set of locations of the acquired surface of the bone and to mathematically connect the first set of locations of the acquired surface of the bone to define the acquired surface the bone.

In some further embodiments, the operations register the acquired surface of the bone in an algorithm for computer assisted navigation during surgery and display a graphical representation of the acquired surface of the bone in a planning view for computer assisted navigation during surgery.

Some further embodiments are directed operations for detecting and treating outlier location(s) of the center of the ball where the ball is not palpating the surface of the bone.

Some further embodiments are directed to acquisition of the anterior and distal surfaces of the femur through palpation using the ball of the ball tip stylus.

Some further embodiments are directed to registering certain landmarks associated with the hip, femur, and/or ankle in an algorithm for computer assisted navigation during surgery.

Some other corresponding embodiments of the present disclosure are directed to a computer program product comprising a non-transitory computer readable medium storing instructions executable by at least one processor for computer assisted navigation during surgery to perform operations. Operations identify locations of fiducials of a reference element on a ball tip stylus in images obtained from tracking cameras with at least partially overlapping field-of-views imaging the ball tip stylus with a ball palpating a surface of a bone. Operations determine locations of a center of the ball based on the locations of the fiducials of the reference element. Operations define an offset-acquired surface of the bone based on mathematically connecting the locations of the center of the ball. Operations determine local normal vectors to the offset-acquired surface for the locations of the center of the ball. Operations translate the offset-acquired surface of the bone toward the surface of the bone along the local normal vectors based on a radius of the ball to define an acquired surface of the bone.

Other system for computer assisted navigation during surgery, computer program products, and related methods for computer assisted navigation during surgery according to embodiments of the inventive subject matter will be or become apparent to one with skill in the art upon review of the following drawings and detailed description. It is intended that all such additional systems, computer program products, and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings:

FIG. 30 illustrates a flowchart of operation that can be performed by at least on processor of a system for computer assisted navigation during surgery in accordance with some embodiments of the present disclosure.

DETAILED DESCRIPTION

Figure 1:
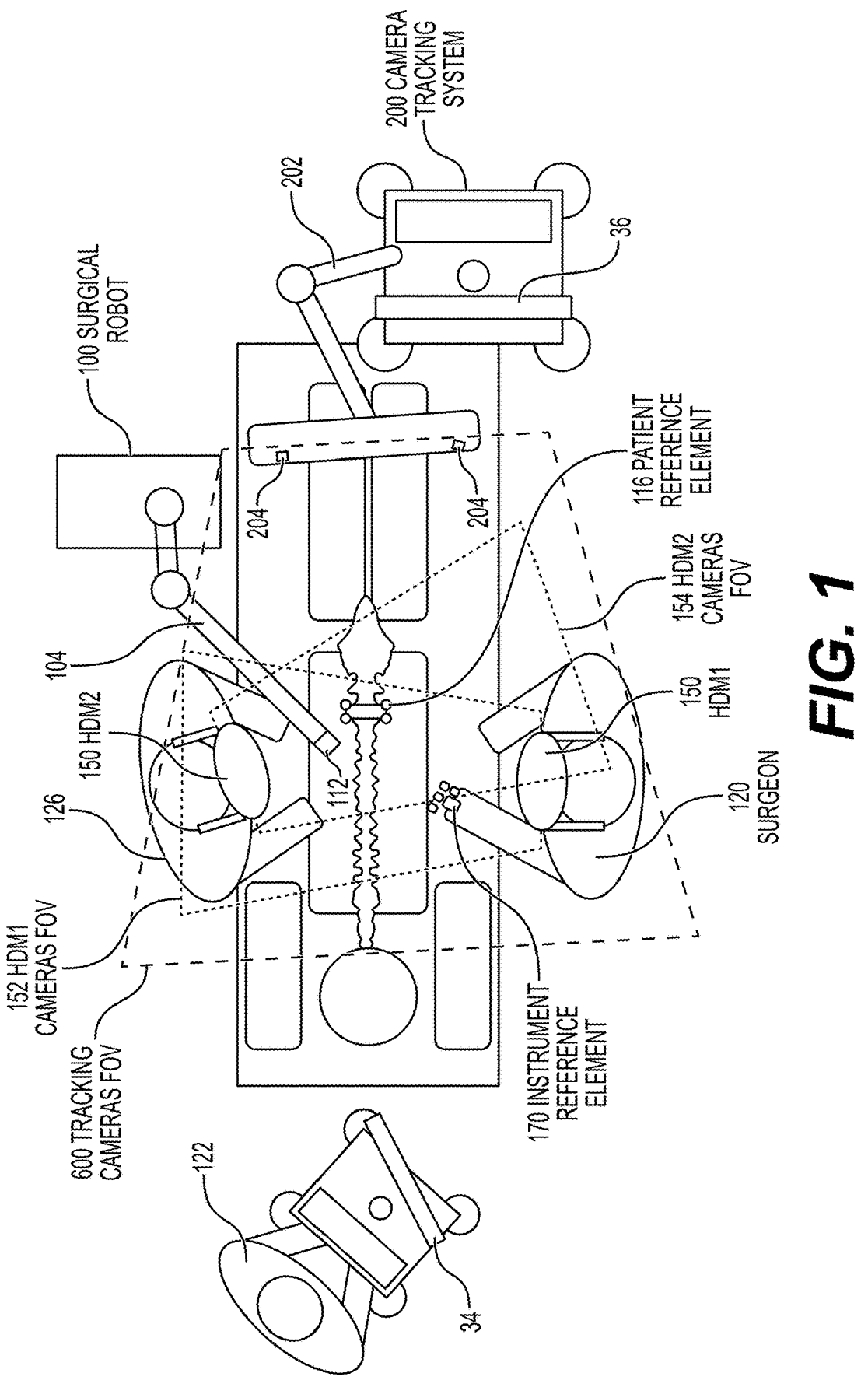
FIG. 1 is an overhead view of a surgical system arranged during a surgical procedure in a surgical room which includes a camera tracking system for computer assisted navigation during surgery and which may further include a surgical robot for robotic assistance according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "attached", "supported," and "coupled" and variations thereof are used broadly and encompass both direct and indirect mountings, connections, attachments, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to a system for computer assisted navigation during surgery which operates with a ball tip stylus used to palpate surfaces of bones during registration of landmarks and other locations in a tracking space of the system. The process of palpating a bone surface using the ball tip stylus is also referred to as "surface painting", and can refer to the user touching, e.g., tapping, the ball to one or more individual surface locations on the bone and/or refer to the user touching and then dragging the ball along while maintaining contact with the bone surface while the stylus is tracked to enable definition of an acquired surface of the bone, in accordance with various embodiments disclosed herein. Before describing these embodiments is detail, various components of a system that may be used with and/or for performing embodiments are described with reference to FIGS. 1-4.

Figure 2:
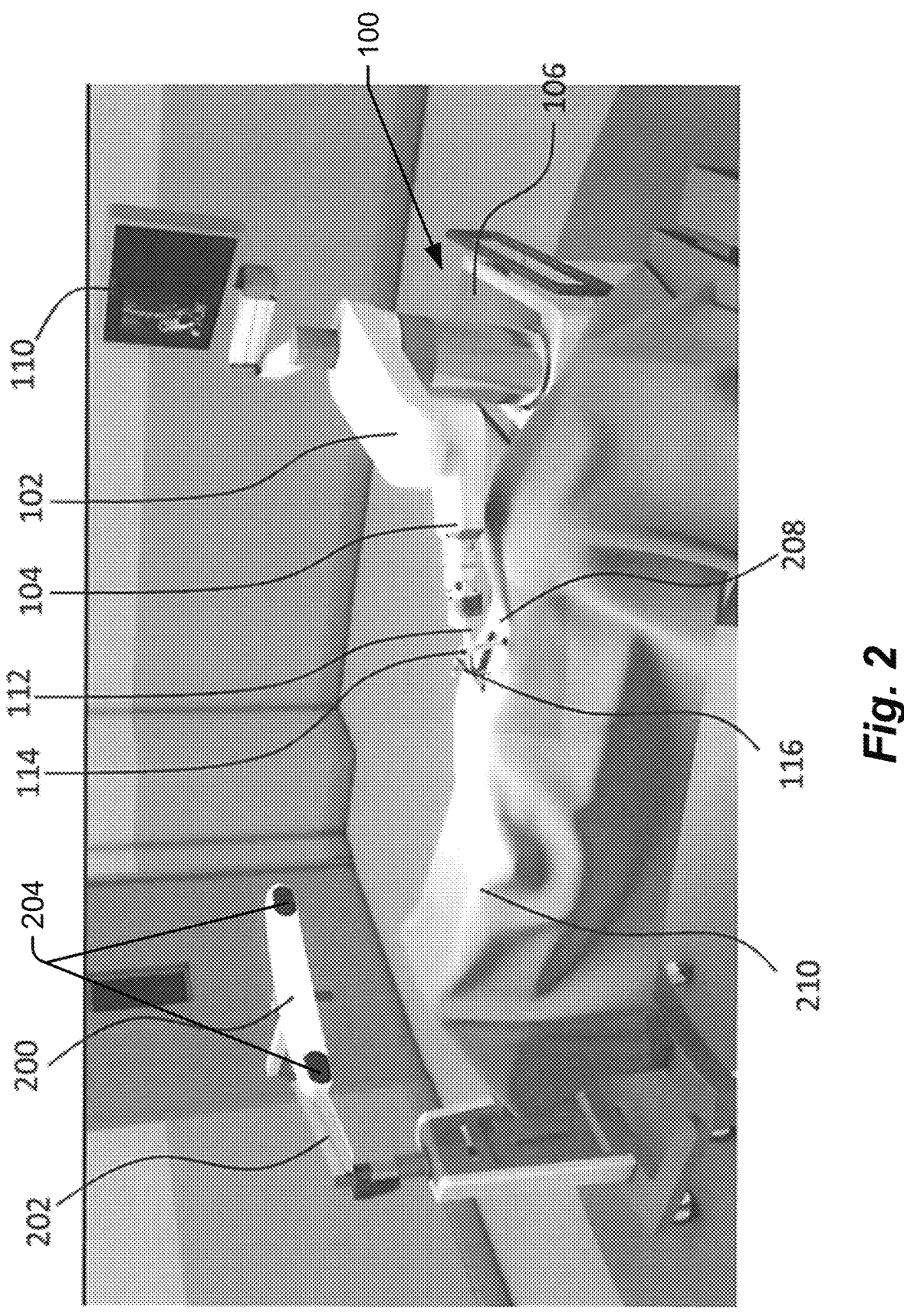
FIG. 2 illustrates the camera tracking system and the surgical robot positioned relative to a patient according to some embodiments.
Figure 3:
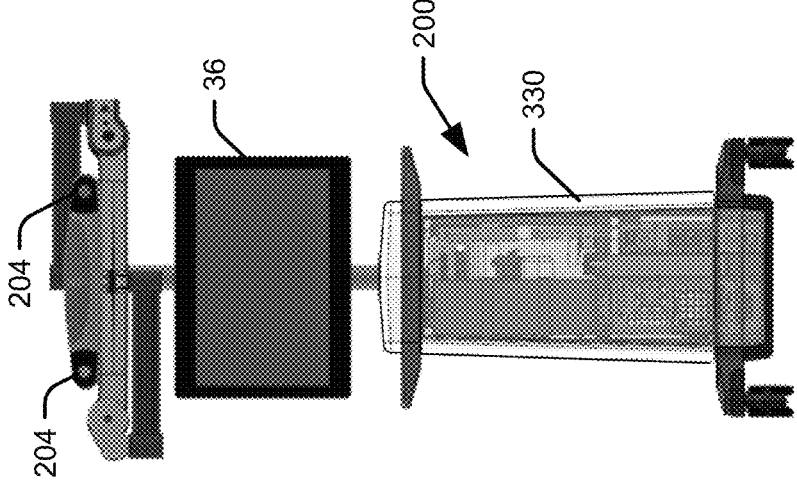
FIG. 3 further illustrates the camera tracking system and the surgical robot configured according to some embodiments.
Figure 3:
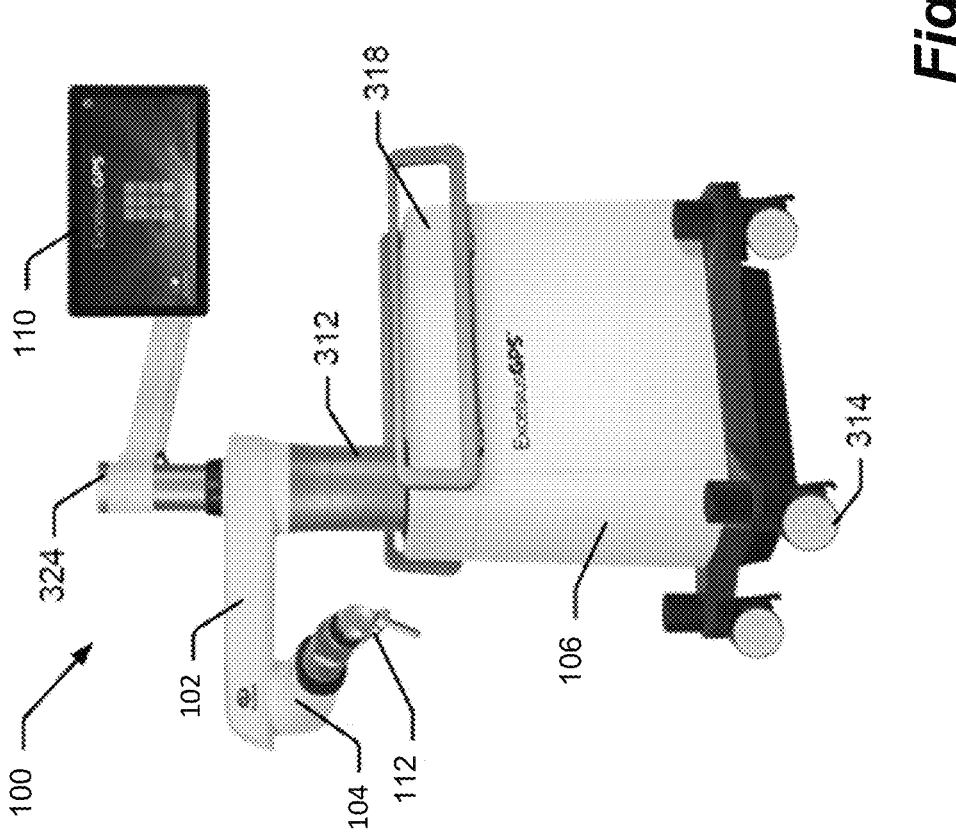
Figure 4:
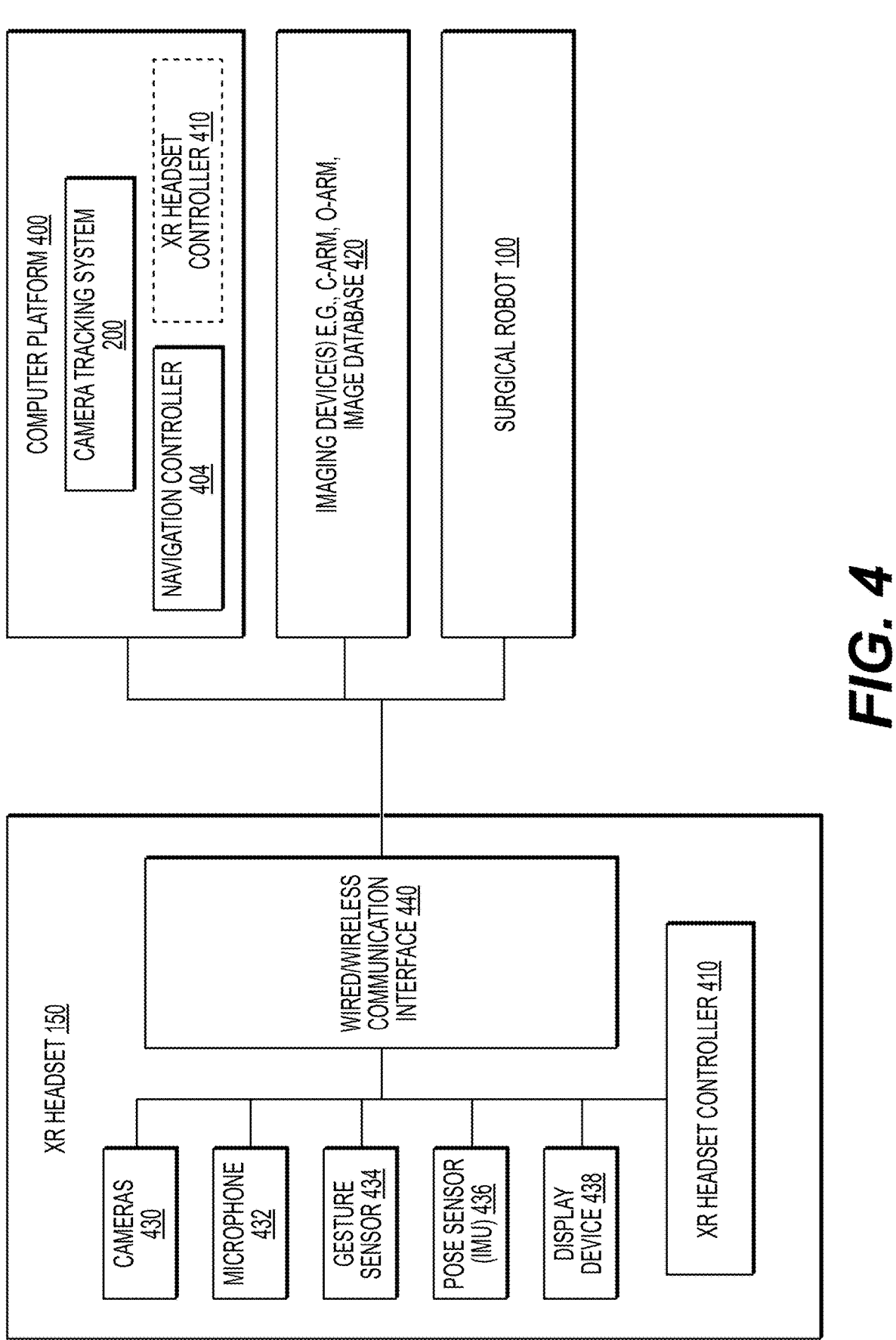
FIG. 4 illustrates a block diagram of a surgical system that includes an extended reality headset, a computer platform, imaging devices, and a surgical robot which are configured to operate according to some embodiments.

FIG. 1 is an overhead view of a surgical system arranged during a surgical procedure in a surgical room. The system includes a camera tracking system 200 for computer assisted navigation during surgery and may further include a surgical robot 100 for robotic assistance according to some embodiments. FIG. 2 illustrates the camera tracking system 200 and the surgical robot 100 positioned relative to a patient according to some embodiments. FIG. 3 further illustrates the camera tracking system 200 and the surgical robot 100 configured according to some embodiments. FIG. 4 illustrates a block diagram of a surgical system that includes an extended reality (XR) headset 150, a computer platform 400, imaging devices 420, and the surgical robot 100 which are configured to operate according to some embodiments.

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset can referred to as an AR headset or a VR headset.

Referring to FIGS. 1-4, the surgical robot 100 may include, for example, one or more robot arms 104, a display 110, an end-effector 112, for example, including a guide tube 114, and an end effector reference element which can include one or more tracking fiducials. A patient reference element 116 (DRB) has a plurality of tracking fiducials and is secured directly to the patient 210 (e.g., to a bone of the patient). A reference element 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual fiducial and pose of an array of fiducials of a reference element.

As used herein, the term "pose" refers to the location (e.g., along 3 orthogonal axes) and/or the rotation angle (e.g., about the 3 orthogonal axes) of fiducials (e.g., DRB) relative to another fiducial (e.g., surveillance fiducial) and/or to a defined coordinate system (e.g., camera coordinate system, navigation coordinate system, etc.). A pose may therefore be defined based on only the multidimensional location of the fiducials relative to another fiducial and/or relative to the defined coordinate system, based on only the multidimensional rotational angles of the fiducials relative to the other fiducial and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking fiducials for single fiducials (e.g., surveillance fiducial) and reference elements which can be formed on or attached to the patient 210 (e.g., patient reference element, DRB, etc.), end effector 112 (e.g., end effector reference element), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the fiducials in order to identify and determine locations of individual fiducials and poses of the reference elements in three-dimensions. For example, active reference elements may include infrared-emitting fiducials that are activated by an electrical signal (e.g., infrared light emitting diodes (LEDs)), and passive reference elements may include retro-reflective fiducials that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance fiducial and poses of reference elements within the XR camera headset field-of-views (FOVs) 152 and 154, respectively. Accordingly, as illustrated in FIG. 1, the location of the surveillance fiducial and the poses of reference elements on various objects can be tracked while in the FOVs 152 and 154 of the XR headsets 150 and/or a FOV 600 of the tracking cameras 204.

FIGS. 1 and 2 illustrate a potential configuration for the placement of the camera tracking system 200 and the surgical robot 100 in an operating room environment. Computer assisted navigated surgery can be provided by the camera tracking system controlling the XR headsets 150 and/or other displays 34, 36, and 110 to display surgical procedure navigation information. The surgical robot 100 is optional during computer assisted navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100 and/or other medical), imaging devices 420 (FIG. 4), and remote sources (e.g., patient medical image database), and/or other electronic equipment. The camera tracking system 200 may track fiducials in 6 degrees-of-freedom (6 DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference element 116 (DRB) is generally rigidly attached to the patient with stable pitch and roll relative to gravity. This local rigid patient reference 116 can serve as a common reference for reference frames relative to other tracked elements, such as a reference element on the end effector 112, instrument reference element 170, and reference elements on the XR headsets 150.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separate from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 includes a guide tube 114, which is configured to receive and orient a surgical instrument, tool, or implant used to perform a surgical procedure on the patient 210. In some other embodiments, the end-effector 112 includes a passive structure guiding a saw blade (e.g., sagittal saw) along a defined cutting plate.

As used herein, the term "end-effector" is used interchangeably with the terms "end-effectuator" and "effectuator element." The term "instrument" is used in a non-limiting manner and can be used interchangeably with "tool"

and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Fiducials of reference elements can be formed on or connected to robot arms 102 and/or 104, the end-effector 112 (e.g., end-effector element 114 in FIG. 2), and/or a surgical instrument (e.g., instrument element 170) to enable tracking of poses in a defined coordinate system, e.g., such as in 6 DOF along 3 orthogonal axes and rotation about the axes. The reference elements enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.
Example Surgical System:

FIG. 4 illustrates a block diagram of a surgical system that includes an XR headset 150, a computer platform 400, imaging devices 420, and a surgical robot 100 which are configured to operate according to some embodiments.

The imaging devices 420 may include a C-arm imaging device, an O-arm imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or of an XR headset controller 410. The surgical system may include the surgical robot 100.

The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100. The navigation information may be displayed through the display device 438 of the XR headset 150 and/or another display device to indicate where the surgical tool and/or the end effector of the surgical robot 100 should be moved to perform a surgical procedure according to a defined surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.
Bone Surface Acquisition Through Palpation ("Painting") Using Ball Tip Stylus:

Various embodiments are directed to registering patient anatomy in an algorithm for computer assisted navigation during surgery through the acquisition of particular landmarks on bones using a process of palpating the surface of the bones with a tracked ball tip stylus. Location of a bone landmark may be acquired and registered by a single touch of the tracked ball tip stylus. A surface of the bone may be acquired and registered by multiple individual touches of, e.g., tapping, the tracked ball tip stylus and/or by touching and then maintaining contact with the surface while moving the ball along the surface, e.g., "painting" the surface while being tracked. Defined landmarks (e.g. most distal and posterior points) can be extracted and other measurements of the bone surface can be performed and concurrently registered for computer assisted navigation. The surface of the bone can be defined (recreated) based on a cloud of points collected by moving the ball of the tracked ball tip stylus on a surface of the bone.

Figure 5:
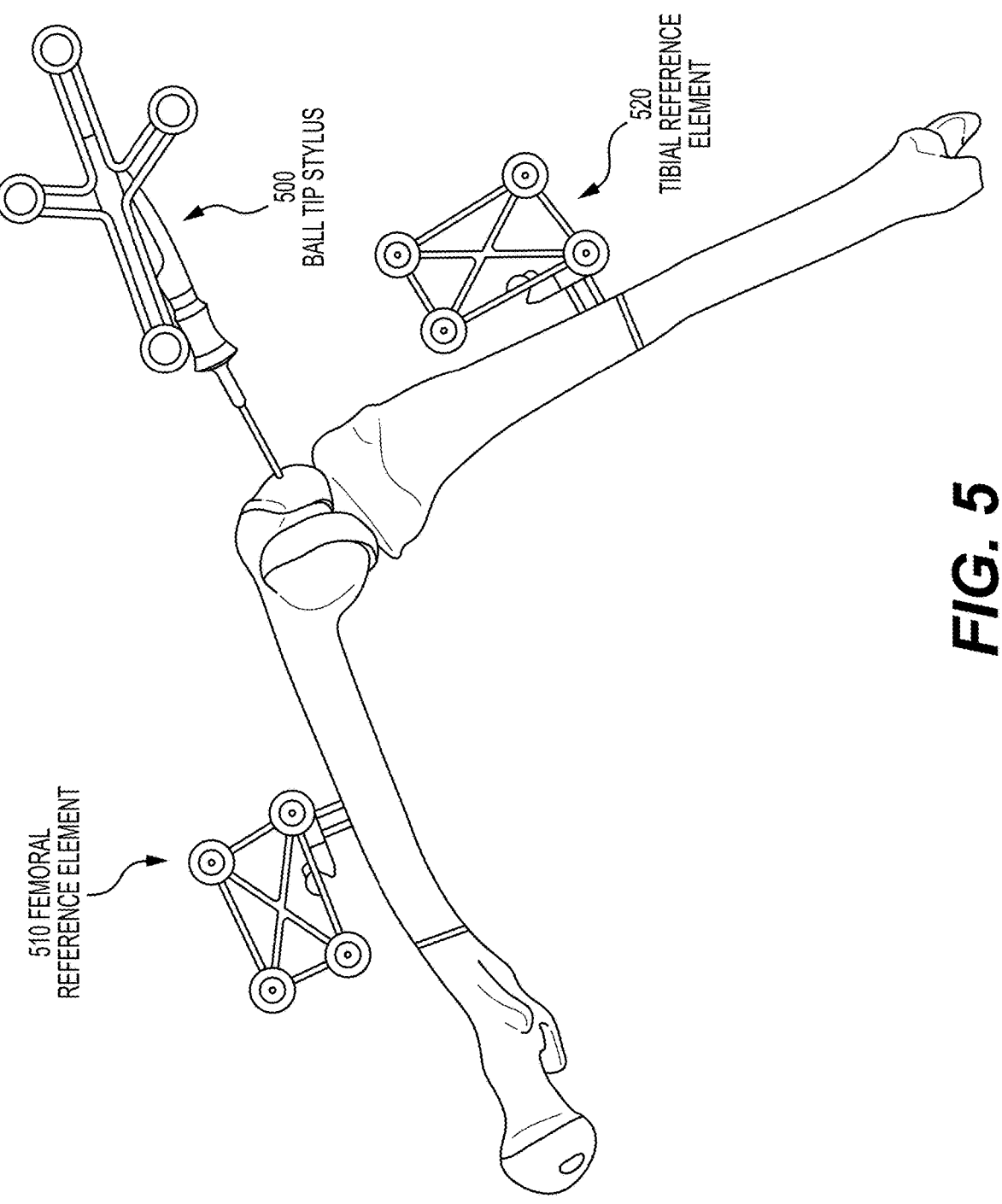
FIG. 5 illustrates a femoral reference element attached to a femur, a tibial reference element attached to a tibia, and a ball tip stylus palpating a bone surface in accordance with some embodiments of the present disclosure.

FIG. 5 illustrates a femoral reference element (reference array having a plurality of tracking markers) 510 attached to a femur, a tibial reference element (reference array having a plurality of tracking markers) 520 attached to a tibia, and a ball tip stylus (a tracked probe having a plurality of tracking markers) 500 palpating a bone surface in accordance with some embodiments of the present disclosure.

Figure 6:
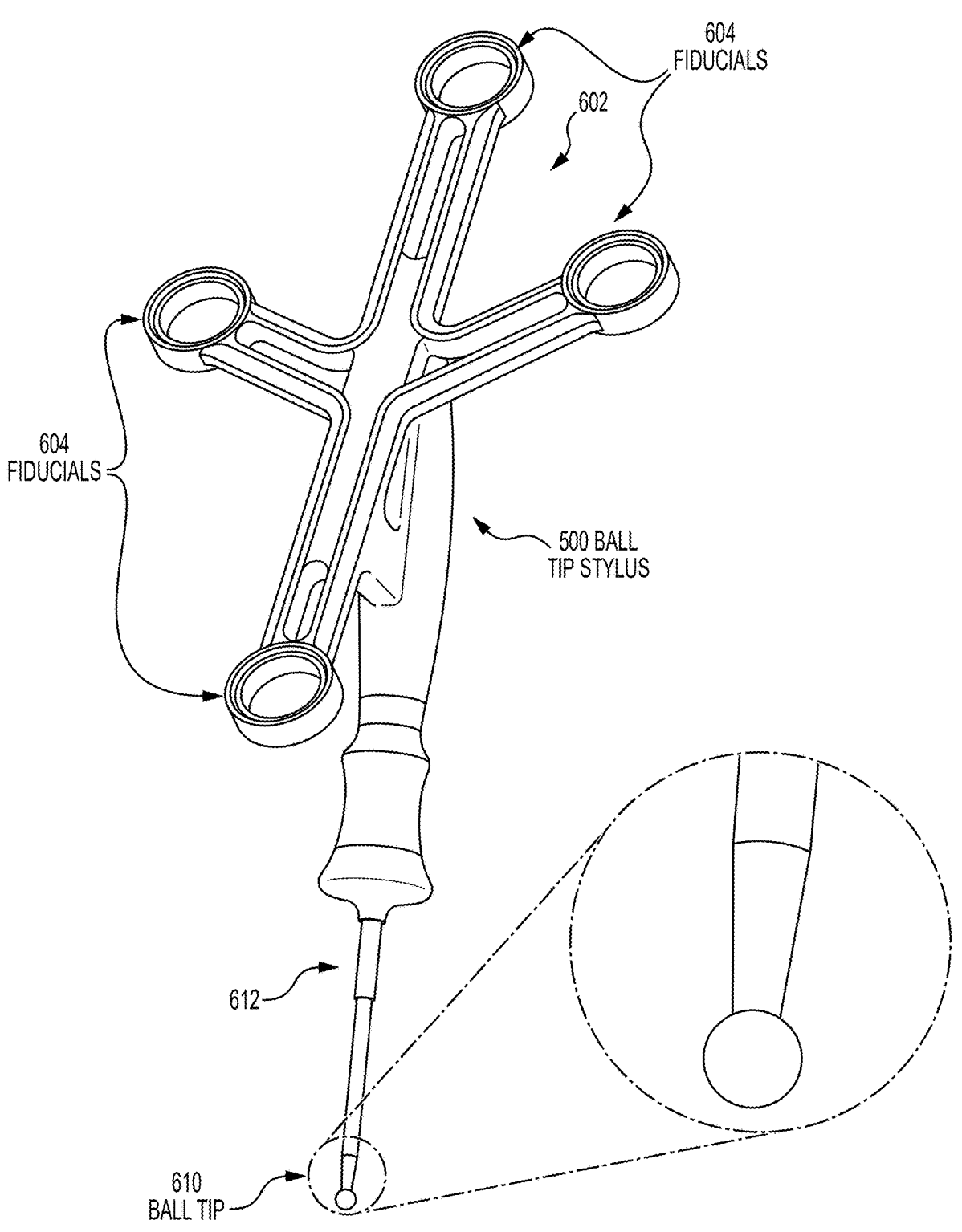
FIG. 6 illustrates the ball tip stylus configured in accordance with some embodiments of the present disclosure.

FIG. 6 illustrates the ball tip stylus 500 configured in accordance with some embodiments of the present disclosure. Referring to FIG. 6, the ball tip stylus 500 includes a ball 610 at a tip that is connected through an interconnecting member 612 to a reference element 602 having an array of fiducials 504. The fiducials 504 may be any shape, such as disks, spheres, etc., may be any color, and may be passive to reflect light or active to emit light.

Tip shape can have a considerable influence on how easy and precisely it is for a user to move the tip across a bone. It has been determined that a ball (spherical) tip glides more easily and consistently on the bone surface but requires taking into account the radius of the tip when defining a location of the surface. The bigger the ball radius is, the easier the gliding capabilities are, but the more difficult it is to access certain areas of a knee joint, especially the posterior aspects of the condyles.

The user, e.g., surgeon, can manipulate the ball 610 of the ball tip stylus 500 to sweep the surface of the bone or cartilage. Doing so, the camera tracking system 200 can measure the location of the ball 610 in a continuous operation and output a cloud of location points. Alternatively, the user can subsequently measure sufficient amount of points by touching them one-by-one with the ball 610 of the ball tip stylus 500 being tracked by the camera tracking system 200.

Figure 7:
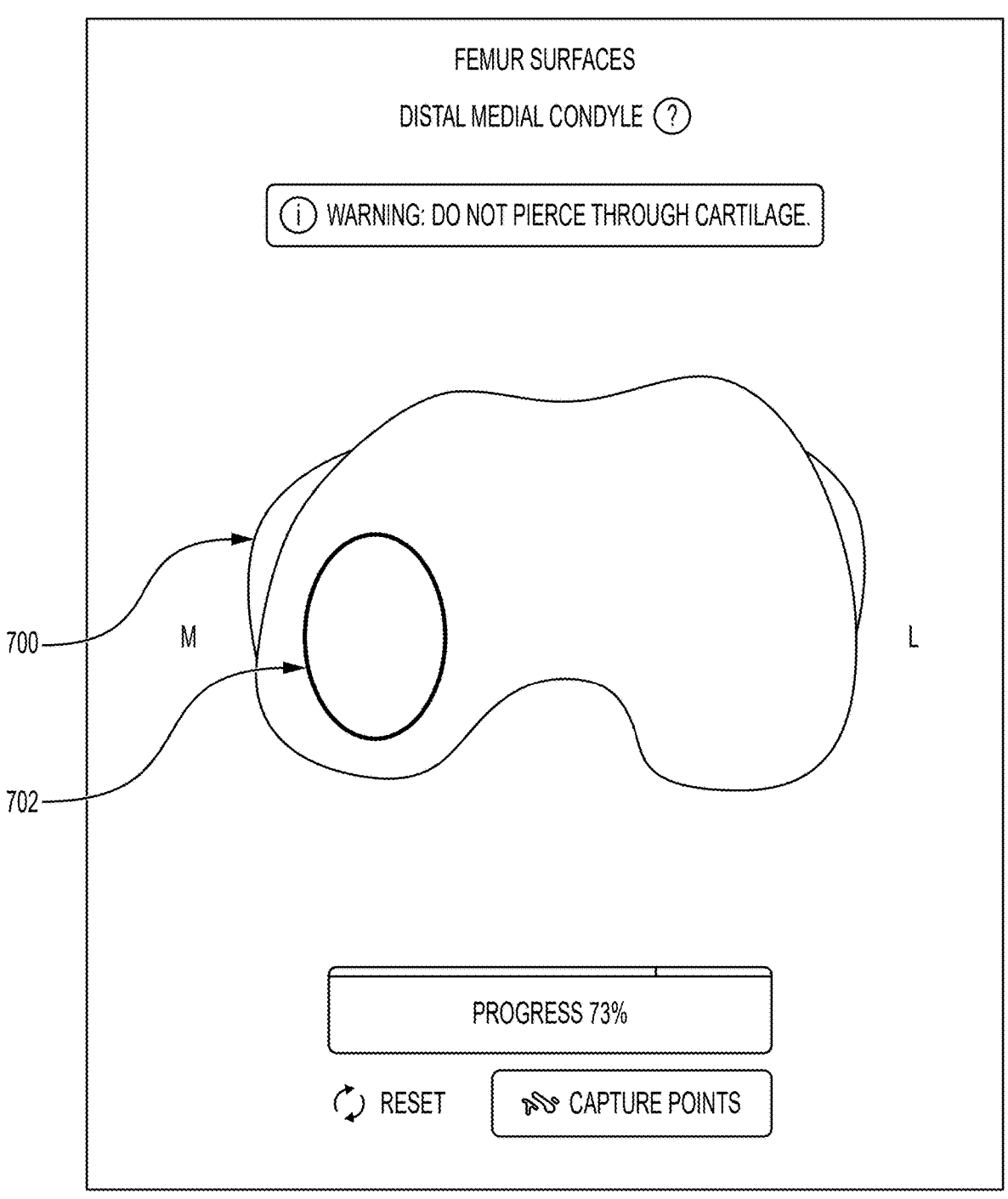
FIG. 7 illustrates a user interface displayed to guide a user through registration of condylar surfaces by palpation using the ball tip stylus in accordance with some embodiments of the present disclosure.

The user may be guided by displayed and/or audible instructions generated by a software application, e.g., algorithm for computer assisted navigation, to acquire a defined surface area of bone(s). FIG. 7 illustrates a user interface that is displayed on a display device to guide a user through registration of condylar surfaces 700 by palpation using the ball tip stylus 500 in accordance with some embodiments of the present disclosure. The user interface displays an indicia 702 to indicate that the user should use the ball tip stylus 500 to palpate the distal medial condyle to cause the system to define a surface of the distal medial condyle and register the surface in an algorithm for computer assisted navigation during surgery.

The locations (points) acquired by the camera tracking system 200 correspond to the center of the ball 610 during the acquisition by the user. The locations can be used to define an offset-acquired surface of the bone. The offset-acquired surface can then be translated to correspond to the actual surface of the bone based on the radius of the ball 610. The system may use a surface matching algorithm for some of these operations.

Figure 8:
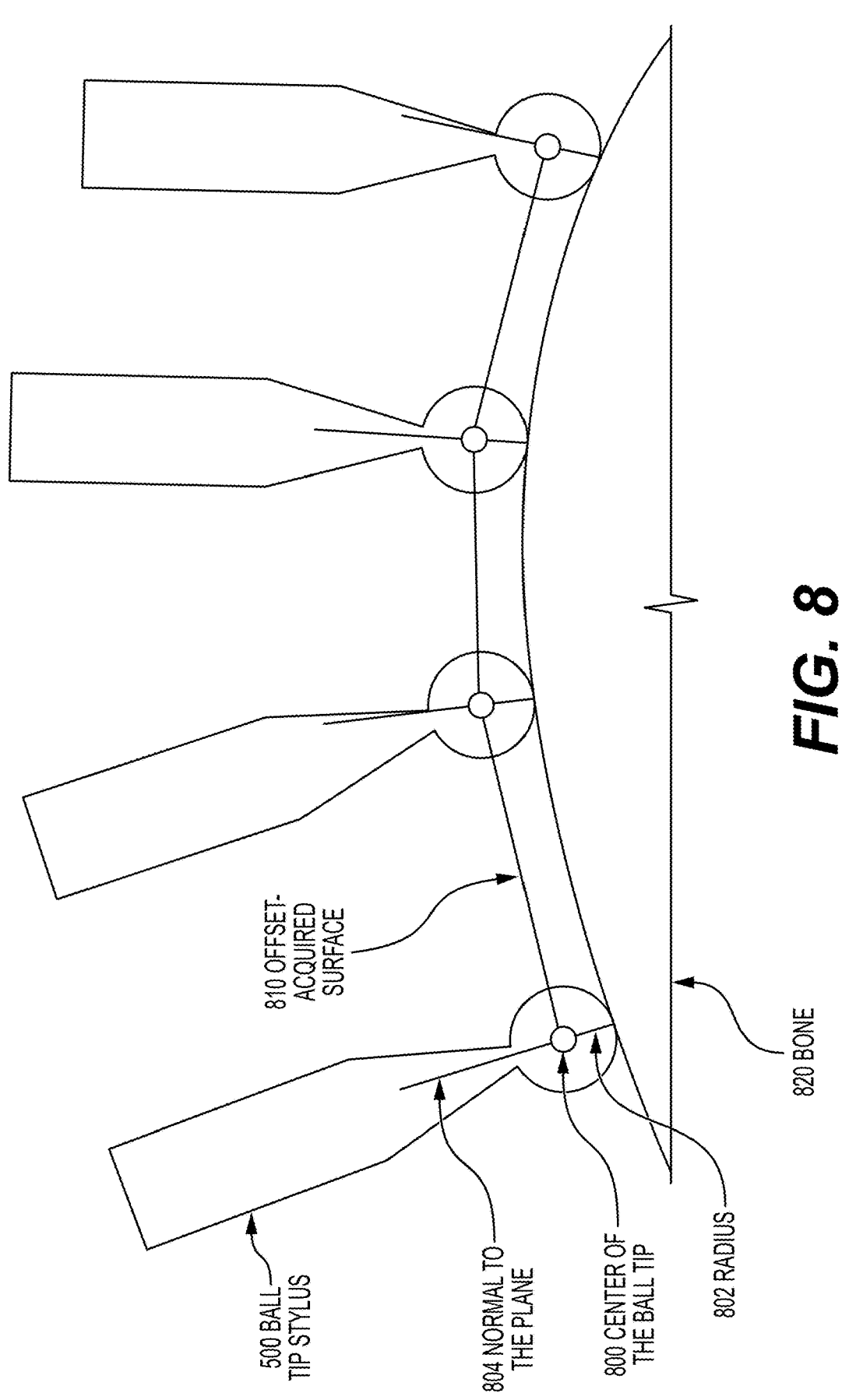
FIG. 8 illustrates a schematic view of operations for defining and then translating an offset-acquired surface of a bone toward the surface of the bone along local normal vectors based on a radius of the ball to define an acquired surface of the bone in accordance with some embodiments of the present disclosure.

FIG. 8 illustrates a schematic view of operations for defining and then translating an offset-acquired surface 810 of a bone 820 toward the surface of the bone 820 along local normal vectors based on a radius of the ball 610 to define an acquired surface of the bone 820 in accordance with some embodiments of the present disclosure. Referring to FIG. 8, in one illustrative embodiment the operations include to acquire locations of the center 800 of the ball 610 as it is used to palpate a surface of the bone 820. The locations of the center 800 of the ball 610 are then mathematically connected together to define an offset-acquired surface 810 of the bone 820, which is offset from the real bone surface by a distance corresponding to the radius 802 of the ball 610. To match the offset-acquired surface 810 to the real bone surface, the operations determine the local normal vector to the real bone surface for each acquired location of the center 800 of the ball 610. The operations then translate each acquired location of the center 800 of the ball 610 along the normal vector toward the bone 820 by a distance corresponding to the radius 802 of the ball 610. These operations enable the surface to be defined in a manner agnostic to the orientation of the ball tip stylus 500, e.g., when not perpendicular to the palpated surface. The acquired surface of the bone, corresponding to the real bone surface, can then be defined by mathematically connecting together the translated locations.

Landmarks relevant for the surgical procedure (e.g. most posterior condylar points and most distal condylar points for femur; most distal points on the plateaux for tibia; etc.) can be extracted for planning and computer assisted navigation. Based on the acquired surface, a registration algorithm can then match patient anatomy with a 3D model of the bone and/or identify additional landmarks for use in planning and computer assisted navigation.

These operations can be more generalized in accordance with some embodiments. FIG. 30 illustrates a flowchart of operation that can be performed by at least on processor of a system for computer assisted navigation during surgery in accordance with some embodiments of the present disclosure.

Referring to FIG. 30, the operations can include to identify 3000 locations of fiducials 504 of a reference element 602 on the ball tip stylus 500 in images obtained from tracking cameras 204 with at least partially overlapping field-of-views imaging the ball tip stylus 500 with the ball 610 palpating (contacting) a surface of the bone 820. The operations determine 3002 locations of the center 800 of the ball 610 based on the locations of the fiducials 504 of the reference element 602. The operations define 3004 an offset-acquired surface 810 of the bone based on mathematically connecting the locations of the center 800 of the ball 610. The operations determine 3006 local normal vectors 804 to the offset-acquired surface 810 for the locations of the center 800 of the ball 610. The operations translate 3008 the offset-acquired surface 810 of the bone 820 toward the surface of the bone 820 along the local normal vectors 804 based on the radius 802 of the ball 610 to define an acquired surface of the bone 820, which ideally corresponds precisely to the real surface of the bone 820.

The operation to translate 3008 the offset-acquired surface 810 of the bone 820 toward the surface of the bone 820 along the local normal vectors 804 based on the radius 802 of the ball 610 to define the acquired surface of the bone 820, may include to translate 3010 the locations of the center 800 of the ball 610 toward the surface of the bone 820 along the local normal vectors 804 by the radius 802 of the ball 610 to define a first set of locations of the acquired surface of the bone 820. The operations may then mathematically connect 3012 the locations of the acquired surface of the bone 820 to define the acquired surface of the bone 820.

As will be explained in further detail below, the operations may further include to register 3014 the acquired surface of the bone 820 in an algorithm for computer assisted navigation during surgery, and/or to display 3016 a graphical representation of the acquired surface of the bone 820 in a planning view for computer assisted navigation during surgery.

Some further embodiments are directed to operations for detecting and treating outlier locations which do not correspond to where the ball 610 is palpating (contacting) the bone 820. During measurement of the bone surface, it may be difficult or not needed to maintain contact with the bone surface. However, without operations to detect and treat such outlier locations, these outlier locations may lead to acquisition of numerous non relevant points, such as while the ball 610 is moved toward the bone 820 to make contact and/or away from the bone 820 for repositioning. In some embodiment, these non-relevant outlier locations are identified using operations that process acquired locations and prevents outlier locations which are space away from the bone surface from being used when defining the offset-acquired surface or acquired surface of the bone. The outlier locations may be identified based comparison to other locations which are determined. For example, when the locations are connected and result in a plane or a curved pathway, any locations which deviate from the plane or pathway by at least a threshold distance can be flagged as outliers.

Corresponding operations for identifying and treating outliers can include, when defining 3004 the offset-acquired surface of the bone 820 based on mathematically connecting the locations of the center 800 of the ball 610, can include to identify among the locations of the center 800 of the ball 610 an outlier location of the center 800 of the ball 610 where the ball 610 is not palpating the surface of the bone 820. The operations can then define 3004 the offset-acquired surface of the bone based 820 on mathematically connecting the locations of the center 800 of the ball 610 without mathematically connecting the outlier location of the center 800 of the ball 610 where the ball 610 is not palpating the surface of the bone.

The operation to identify among the locations of the center 800 of the ball 610 an outlier location of the center 800 of the ball 610 where the ball 610 is not palpating the surface of the bone 820, may include to identify the outlier location of the center 800 of the ball 610 where the ball 610 is not palpating (contacting) the surface of the bone 820 based on the outlier location of the center 800 of the ball 610 having at least a first threshold distance, in a direction along the local normal vector 804 to the offset-acquired surface 810, from other ones of the locations of the center 800 of the ball 610 which are within a second threshold distance in a direction along the offset-acquired surface 810.

Some further embodiments are directed to operations for acquisition of posterior and other features of the condylar surfaces.

Figure 9:
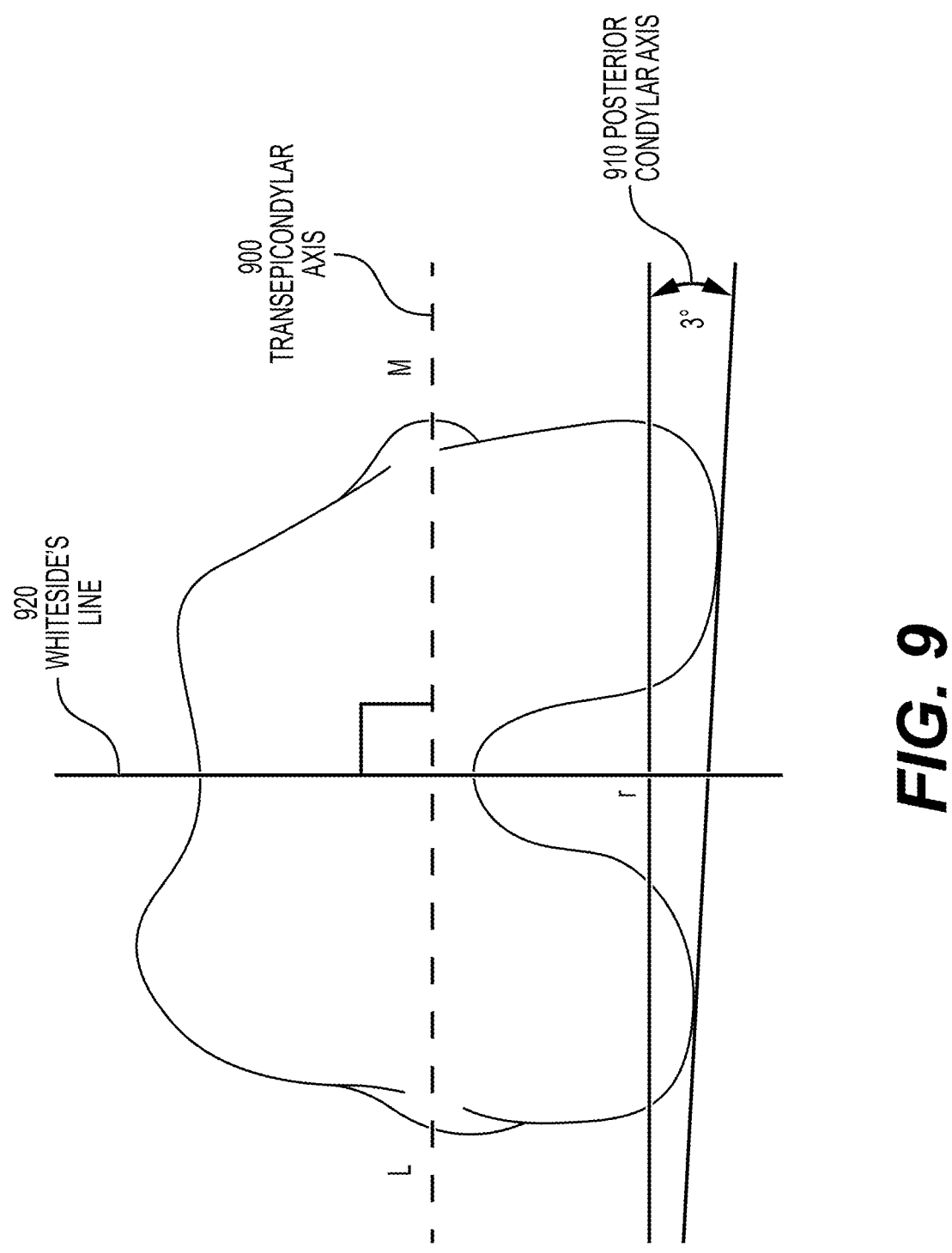
FIG. 9 illustrates a schematic view of operations for acquiring femoral and/or tibial features in accordance with some embodiments of the present disclosure.

FIG. 9 illustrates a schematic view of operations for acquiring femoral and/or tibial features in accordance with some embodiments of the present disclosure. Referring to FIG. 9, acquisition of features and other landmarks on the anterior and distal surfaces of the femur as well as tibial plateau through palpation can be performed with the ball tip stylus 500. For example, these areas are naturally exposed, such for the femur, or can be easily accessed, such as by hyperflexion of the joint which provides easy access of about 75% of the tibial plateau. However, the posterior aspect of the condylar surfaces are difficult to acquire through palpation with appropriate level of usability. From a clinical perspective, acquisition of the posterior condylar aspect may be required to determine the posterior condylar axis 910 which is one option to set femoral component internal and/or external rotation during planning.

Operations disclosed here may be used to acquire a posterior aspect of the condylar surfaces using the White-side's line 920 and/or the transepicondylar axis 900.

Two alternative operational approaches may be used acquisition of this particular area.

The first operational approach uses two steps of acquisition. In one step, landmarks on the anterior and distal surfaces of femur are acquired and partial registration of the femur is performed. Acquisition of the tibial plateau and full registration of the tibia is performed. Tibial resection is performed. Then, in another step acquisition of the posterior surface of the femoral condyles is performed.

For the first operational approach, in the context of FIG. 30 the acquired surface of the bone can define anterior and distal surfaces of a femur palpated by the ball 610. Corresponding operations for one of the steps can include to acquire locations (e.g., 3000-3008 in FIG. 30) of a tibial plateau based on locations of the anterior and distal surfaces of the femur defined by the acquired surface of the bone. The locations of the tibia in a tracking space can be registered (e.g., 3014 in FIG. 30) based on the acquired locations of the tibial plateau. Corresponding operations for the other one of the steps can include to, following tibial resection, the operations identify locations of the fiducials 504 of the reference element 602 on the ball tip stylus 500 in further images obtained from the tracking cameras 204 imaging the ball tip stylus 500 with the ball 610 palpating (contacting) a posterior surface of femoral condyles. The operations determine locations of the center of the ball 610 based on the locations of the fiducials of the reference element, and define an offset-acquired surface of the posterior surface of femoral condyles based on mathematically connecting the locations of the center of the ball 610. The operations determine local normal vectors to the offset-acquired surface of the posterior surface of the femoral condyles for the locations of the center of the ball 610, and translate the offset-acquired surface of the posterior surface of femoral condyles toward the posterior surface of femoral condyles along the local normal vectors based on the radius of the ball 610 to define an acquired surface of the posterior surface of femoral condyles.

Figure 10:
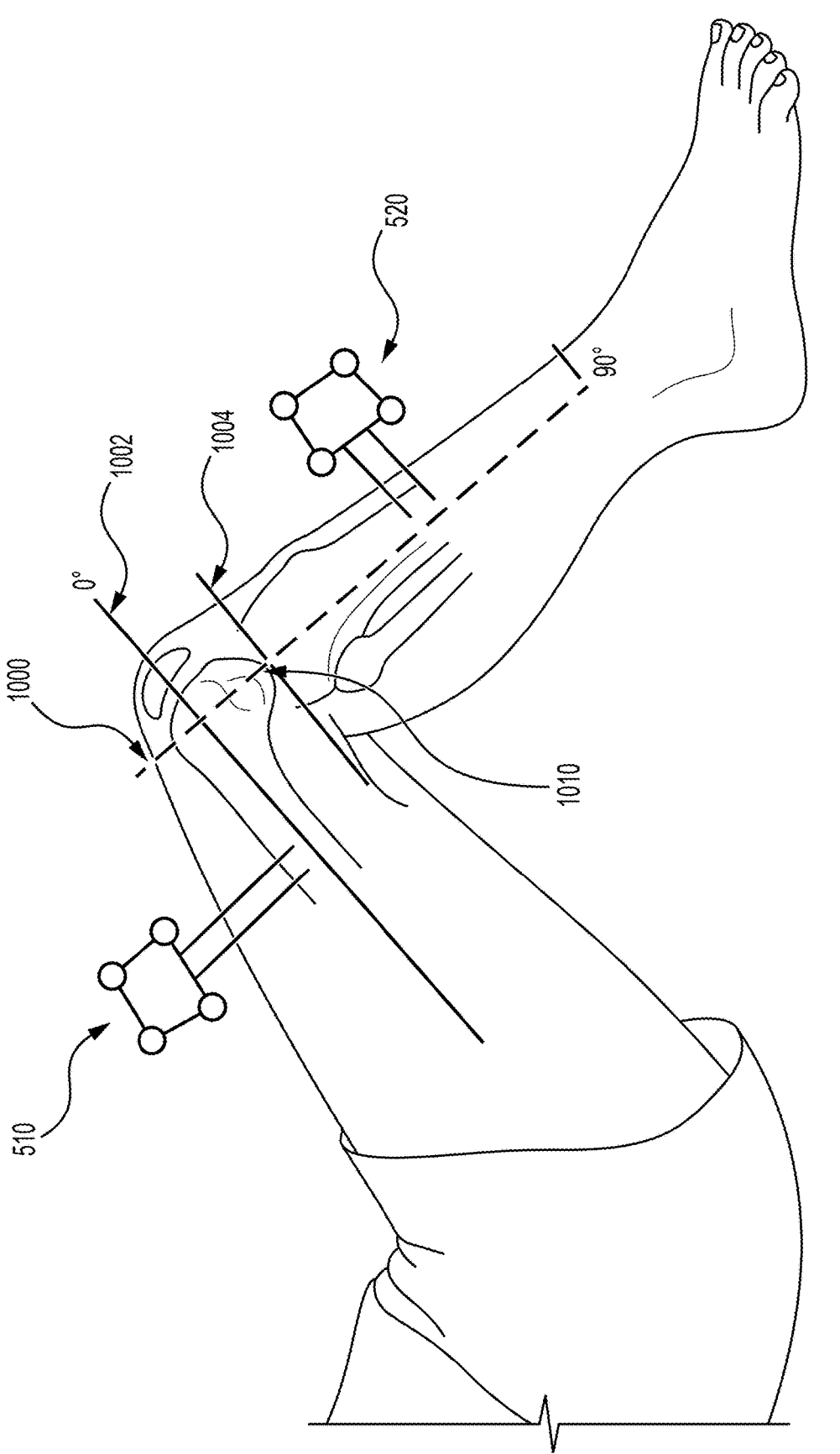
FIG. 10 illustrates a schematic view of alternative structure and operations for acquiring femoral and/or tibial features in accordance with some embodiments of the present disclosure.

The second operational approach can use the registered tibia with its reference element 520 as a navigated instrument to acquire the posterior condylar axis. FIG. 10 illustrates a schematic view of structure and operations that may be used for the second operational approach for acquiring femoral and/or tibial features. In FIG. 10, a virtual plane 1002 is illustrated as being attached to the femur and determined using landmarks such as a mechanical axis and superior distal aspect of the femur. Another virtual plane 1004 is illustrated as being attached to the tibia and determined from landmarks, such as the mechanical axis and proximal geometry. Another virtual plate 1000 extends perpendicular to the virtual plane 1002 through the tibia to intersect the virtual plane 1004. The intersection of the virtual planes 1000 and 1004 is illustrated as occurring at location 1010, which corresponds to acquisition of the posterior condylar axis using the registered tibia bone.

Corresponding operations can include to acquire locations (e.g., 3000-3008 in FIG. 30) of a tibial plateau based on locations of the anterior and distal surfaces of the femur defined by the acquired surface of the bone. The locations of the tibia in a tracking space can be registered (e.g., 3014 in FIG. 30) based on the acquired locations of the tibial plateau. The operations identify locations of fiducials of the tibial reference element 520 attached to the tibia and locations of fiducials of the femoral reference element 510 attached to the femur in images obtained from the tracking cameras 204 while the ball 610 is palpating the femur. The operations acquire location of the posterior condylar axis based on the registered locations of the tibia and based on the identified locations of the fiducials of the tibial reference element 520 and the femoral reference element 510.

The operation to acquire location of the posterior condylar axis based on the registered locations of the tibia and based on the identified locations of the fiducials of the tibial reference element 520 and the femoral reference element 510, can include to determine a distal femoral plane to be virtually attached to the femur and pass through a posterior surface of femoral condyles. The operations can acquire locations of a tibial plateau based on locations of the anterior and distal surfaces of the femur defined by the acquired surface of the bone and based on the identified locations of the fiducials of the tibial reference element 520. The operations can determine a proximal tibial plane which is virtually attached to the tibia, and determine a posterior condylar axis based on tracking movement of locations of the fiducials of the tibial reference element 520 relative to locations of the fiducials of the femoral reference element 510 as the tibia is rotated relative to the femur.

The operation to determine the posterior condylar axis based on tracking movement of locations of the fiducials of the tibial reference element 520 relative to locations of the fiducials of the femoral reference element 510 as the tibia is rotated relative to the femur, can include to determine the posterior condylar axis based on identifying location of intersection of the distal femoral plane and the proximal tibial plane.

The operation to determine the distal femoral plane can include to determine the distal femoral plane to be normal to a femoral mechanical axis, virtually attached to the femur, and pass through the posterior surface of femoral condyles.

Some further embodiments are directed to operations for use of bone palpation in a patient registration workflow. FIGS. 11-29 illustrate user interfaces that can be displayed to guide a user through operations for registration of surface features, including using the ball tip stylus 500, in accordance with some embodiments of the present disclosure. It is to be understood that although the user interfaces and associated operations are described as being performed in a certain sequence, they may be performed in other sequences while still being within disclosed embodiments. Moreover, it is not necessary that all of the user interfaces and/or described operations be performed. Instead, fewer operations may be performed while still being within disclosed embodiments.

During a patient registration procedure, landmarks used to register patient anatomy can be extracted using either single point palpation collection or surface painting (point cloud). The user interfaces shown in FIGS. 11-28 illustrate graphical representations of certain landmarks that may be displayed to guide a user through patient registration.

Figure 11:
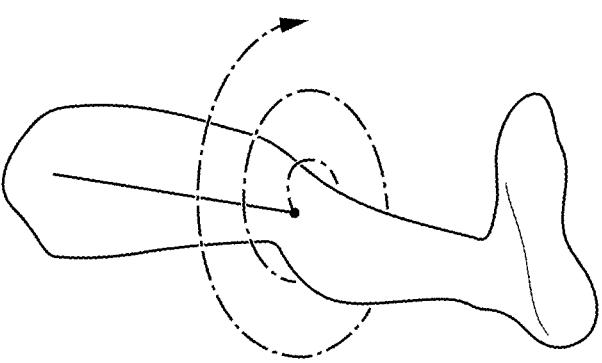
FIGS. 11-29 illustrate user interfaces that can be displayed to guide a user through operations for registration of surface features, including using the ball tip stylus, in accordance with some embodiments of the present disclosure.
Figure 15:
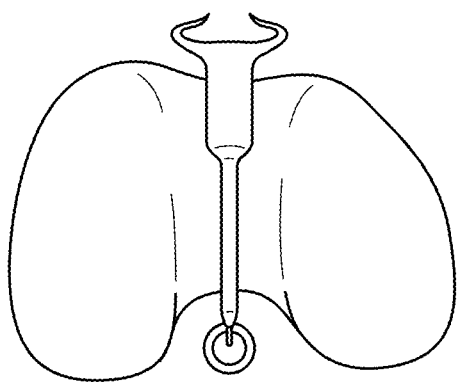

In FIG. 11 operations display in a planning view for computer assisted navigation during surgery the location of hip center. The operations may acquire location of hip center based on tracking movement of locations of fiducials of a tibial reference element 520 attached to a tibia during rotation of the tibia. In FIG. 15, operations display the location of the Whiteside's line. The operations can acquire location of a Whiteside's line based on determining location of the center of the ball palpating a femur surface location corresponding to the Whiteside's line. The operations can register in an algorithm for computer assisted navigation during surgery, the location of hip center and the location of the Whiteside's line.

Figure 12:
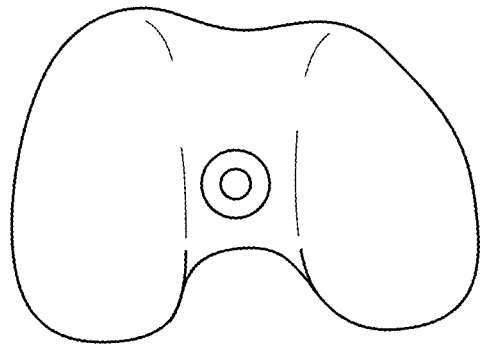
Figure 13:
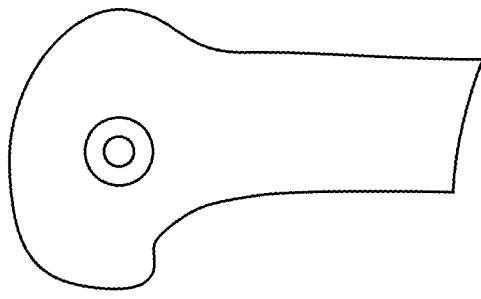

In FIG. 12 operations can display in a view for computer assisted navigation during surgery, a graphical representation of the femoral condyles with an indication for a user to acquire the location of the femoral distal mechanical axis point and/or which is dynamically updated to indicate locations that have been acquired through palpation using the ball tip stylus 500. In FIG. 13 operations can display in another view a graphical representation of the femoral medial condyles with an indication for the user to acquire the location of the femoral medial epicondyle and/or which is dynamically updated to indicate locations that have been acquired through palpation using the ball tip stylus 500.

Figure 14:
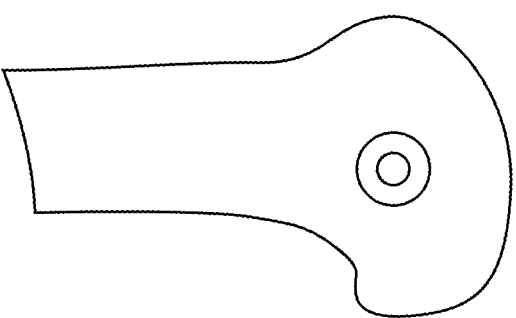
Figure 16:
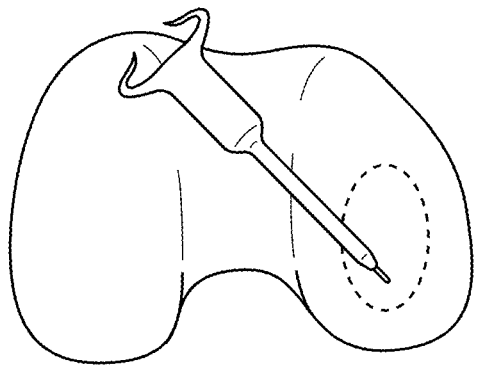
Figure 17:
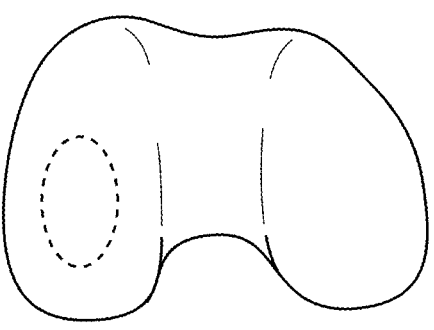

In FIG. 14 operations can display a graphical representation of the femoral lateral condyles with an indication for the user to acquire the location of the femoral lateral epicondyle and/or which is dynamically updated to indicate locations that have been acquired through palpation using the ball tip stylus 500. In FIG. 16 operations can display a graphical representation of the femoral condyles with an indication for the user to acquire the location of the femoral medial distal condylar point and/or which is dynamically updated to indicate locations that have been acquired through palpation using the ball tip stylus 500. In FIG. 17 operations can display a graphical representation of the femoral condyles with an indication for the user to acquire the location of the femoral lateral distal condylar point and/or which is dynamically updated to indicate locations that have been acquired through palpation using the ball tip stylus 500.

Figure 18:
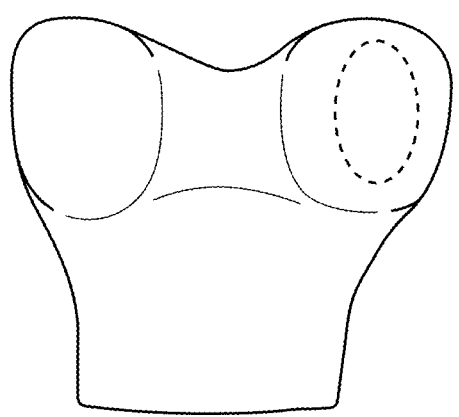
Figure 19:
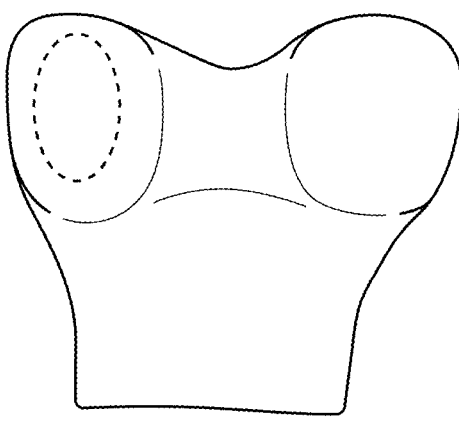
Figure 20:
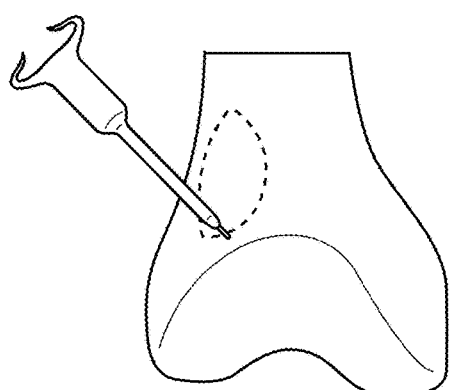

In FIG. 18 operations can display a graphical representation of the femoral condyles with an indication for the user to acquire the location of the femoral medial posterior condylar point which is to be palpated by the user and/or which is dynamically updated to indicate locations that have been acquired through palpation using the ball tip stylus 500. In FIG. 19 operations can display a graphical representation of the femoral condyles with an indication for the user to acquire the location of the femoral lateral posterior condylar point and/or which is dynamically updated to indicate locations that have been acquired through palpation using the ball tip stylus 500. In FIG. 20 operations can display a graphical representation of the femoral condyles with an indication for the user to acquire the location of the femoral anterior reference surface and/or which is dynamically updated to indicate locations that have been acquired through palpation using the ball tip stylus 500.

Corresponding operations can include to acquire location of a femoral distal mechanical axis point based on determining location of the center of the ball palpating a surface between the femoral condyles. Another operation can include to acquire location of a femoral medial epicondyle based on determining location of the center of the ball palpating a femur surface location corresponding to the femoral medial epicondyle. Another operation can include to acquire location of a femoral lateral epicondyle based on determining location of the center of the ball palpating a femur surface location corresponding to the femoral lateral epicondyle. Another operation can include to acquire location of a femoral medial distal condylar point based on determining a most distal location of an acquired surface of the femoral medial distal condylar palpated by the ball. Another operation can include to acquire location of a femoral lateral distal condylar point based on determining a most distal location of an acquired surface of the femoral lateral distal condylar palpated by the ball. Another operation can include to acquire location of a femoral medial posterior condylar point based on determining a most posterior location of an acquired surface of the femoral medial posterior condylar palpated by the ball. Another operation can include to acquire location of a femoral lateral posterior condylar point based on determining a most posterior location of an acquired surface of the femoral lateral posterior condylar palpated by the ball. Another operation can include to acquire location of a femoral anterior reference surface based on determining locations of an acquired surface of the femoral anterior reference surface palpated by the ball.

The operations may register in an algorithm for computer assisted navigation during surgery, the location of the femoral distal mechanical axis point, the location of the femoral medial epicondyle, the location of the femoral lateral epicondyle, the location of the femoral medial distal condylar point, the location of the femoral lateral distal condylar point, the location of the femoral medial posterior condylar point, the location of the femoral lateral posterior condylar point, and the location of the femoral anterior reference surface.

Figure 21:
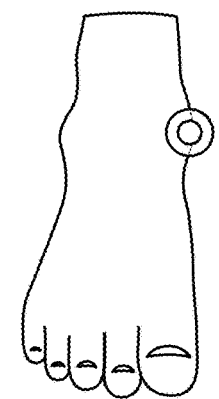
Figure 22:
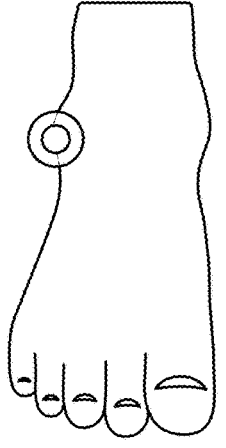
Figure 23:
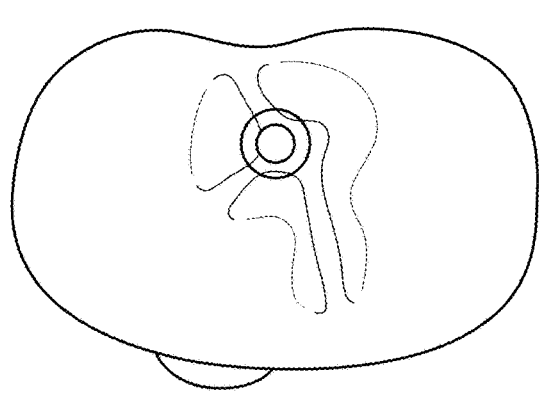

In FIG. 21 operations can display a graphical representation of an ankle with an indication for a user to acquire the location of the ankle medial melleolus point and/or which is dynamically updated to indicate locations that have been acquired through palpation using the ball tip stylus 500. In FIG. 22 operations can display a graphical representation of an ankle with an indication for a user to acquire the location of the ankle lateral melleolus point and/or which is dynamically updated to indicate locations that have been acquired through palpation using the ball tip stylus 500. In FIG. 23 operations can display a graphical representation of the femoral condyles with an indication for the user to acquire the location of the tibial proximal mechanical axis point and/or which is dynamically updated to indicate locations that have been acquired through palpation using the ball tip stylus 500.

Figure 24:
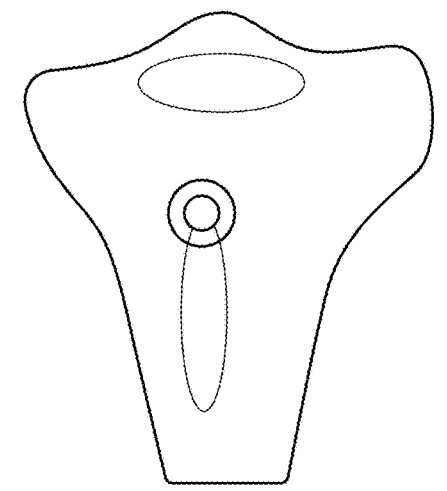
Figure 25:
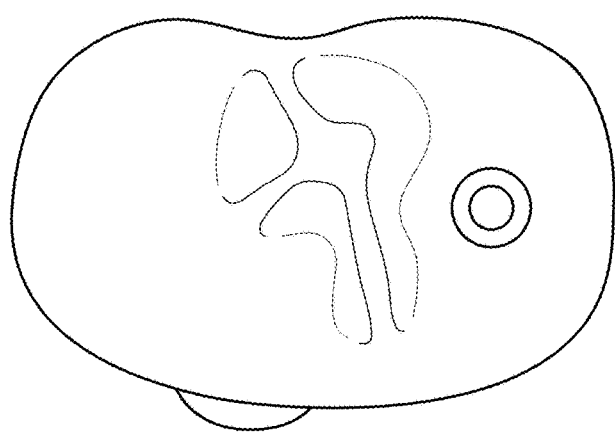
Figure 26:
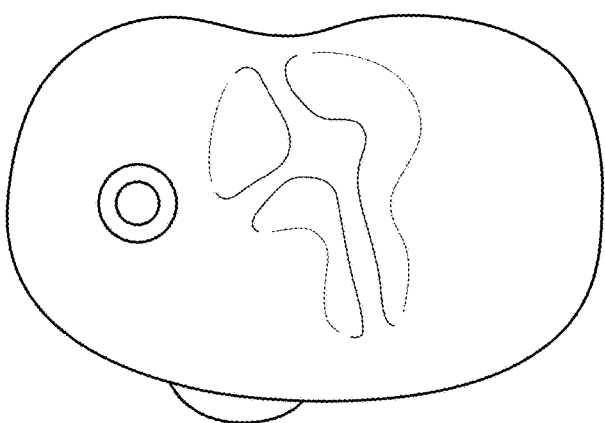
Figure 27:
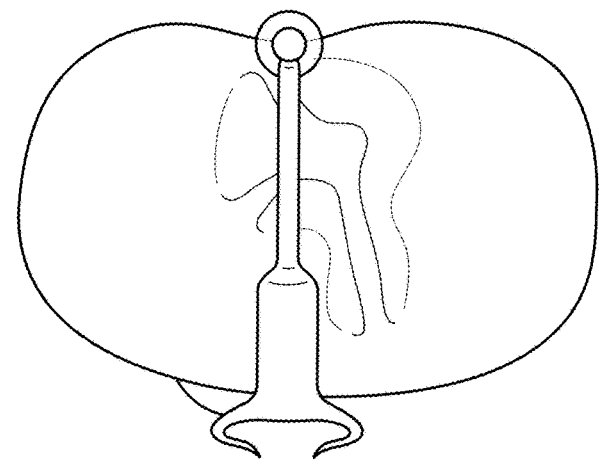
Figure 28:
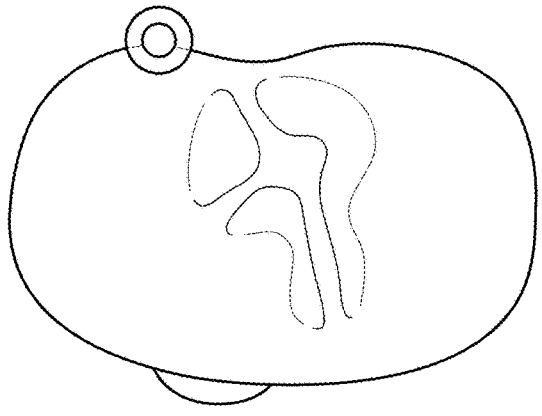

In FIG. 24 operations can display a graphical representation of the femoral condyles with an indication for the user to acquire the location of the tibial anterior reference point and/or which is dynamically updated to indicate locations that have been acquired through palpation using the ball tip stylus 500. In FIG. 25 operations can display a graphical representation of the femoral condyles with an indication for the user to acquire the location of the tibial medial plateau point and/or which is dynamically updated to indicate locations that have been acquired through palpation using the ball tip stylus 500. In FIG. 26 operations can display a graphical representation of the femoral condyles with an indication for the user to acquire the location of the tibial lateral plateau point and/or which is dynamically updated to indicate locations that have been acquired through palpation using the ball tip stylus 500. In FIG. 27 operations can display a graphical representation of the femoral condyles with an indication for the user to acquire the location of the tibial anterior-posterior line. In FIG. 28 operations can display a graphical representation of the femoral condyles with an indication for the user to acquire the location of the tibial posterior point and/or which is dynamically updated to indicate locations that have been acquired through palpation using the ball tip stylus 500

Corresponding operations can include to define a femoral anterior reference surface based on the acquired surface being defined for a femoral anterior surface palpated by the ball. Another operation can include to acquire location of an ankle medial melleolus point based on determining location of the center of the ball palpating an ankle surface location corresponding to the ankle medial melleolus point. Another operation can include to acquire location of an ankle lateral melleolus point based on determining location of the center of the ball palpating an ankle surface location corresponding to the ankle lateral melleolus point. Another operation can include to acquire location of a tibial proximal mechanical axis point based on determining location of the center of the ball palpating a tibia location corresponding to the tibial proximal mechanical axis point. Another operation can include to acquire location of a tibial anterior reference point based on determining location of the center of the ball palpating a tibia location corresponding to the tibial anterior reference point. Another operation can include to acquire location of a tibial medial plateau point based on determining location of the center of the ball palpating a tibia location corresponding to the tibial medial plateau point. Another operation can include to acquire location of a tibial lateral plateau point based on determining location of the center of the ball palpating a tibia location corresponding to the tibial lateral plateau point. Another operation can include to acquire location of a tibial anterior-posterior line based on determining location of the locations of fiducials of a reference element while the ball tip stylus is oriented corresponding to the tibial anterior-posterior line while the ball is palpating a tibia location corresponding to the tibial anterior-posterior line. Another operation can include to acquire location of a tibial posterior point based on determining location of the center of the ball palpating a tibia location corresponding to the tibial posterior point.

The operations may register in an algorithm for computer assisted navigation during surgery, the defined femoral anterior reference surface, the location of the ankle medial melleolus point, the location of the ankle lateral melleolus point, the location of the tibial proximal mechanical axis point, the location of the tibial anterior reference point, the location of the tibial medial plateau point, the location of the tibial lateral plateau point, the location of the tibial anterior-posterior line, and the location of the tibial posterior point.

The operations may display in a planning view of the algorithm for computer assisted navigation during surgery, the defined femoral anterior reference surface, the location of the ankle medial melleolus point, the location of the ankle lateral melleolus point, the location of the tibial proximal mechanical axis point, the location of the tibial anterior reference point, the location of the tibial medial plateau point, the location of the tibial lateral plateau point, the location of the tibial anterior-posterior line, and the location of the tibial posterior point.

Figure 29:
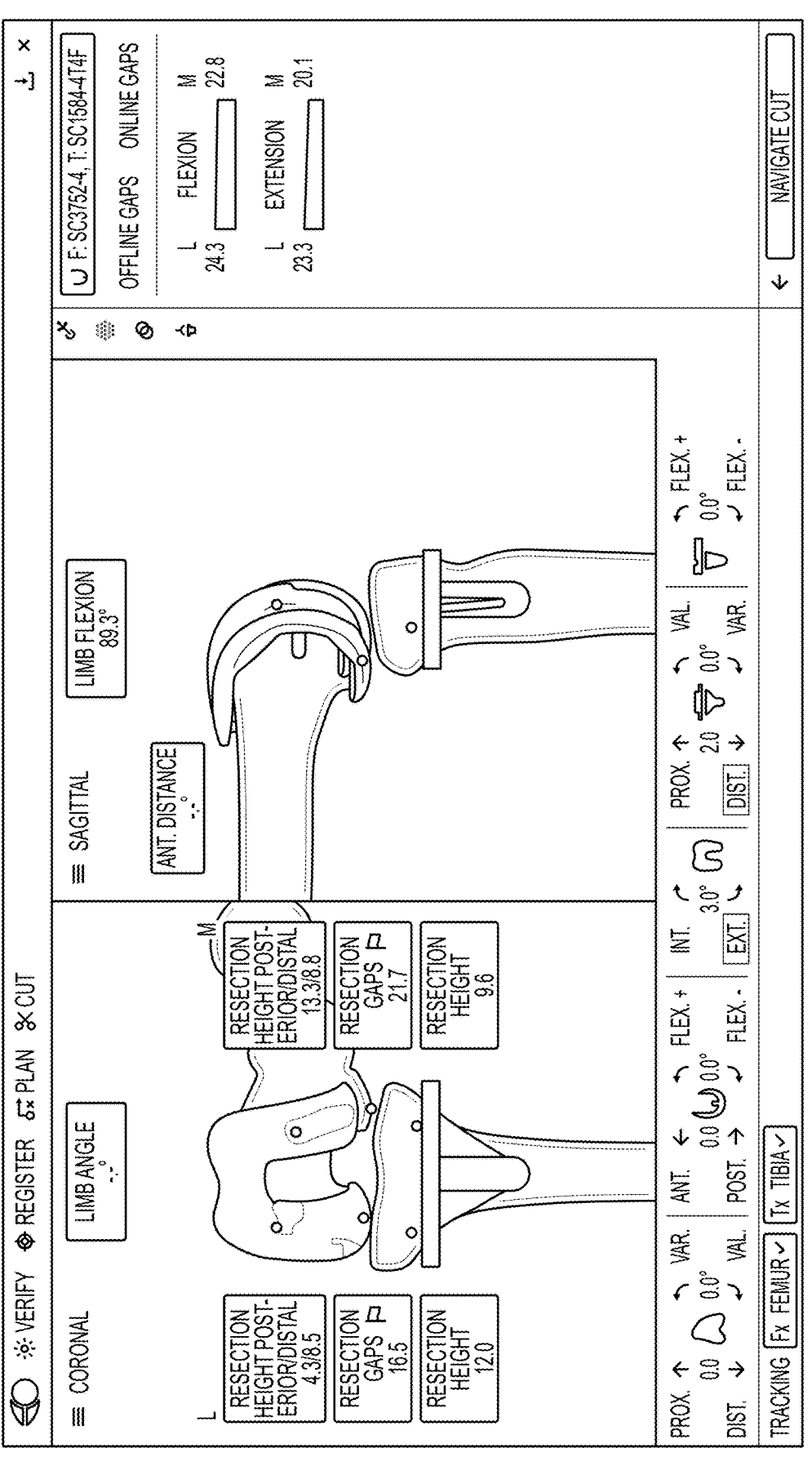

FIG. 29 illustrates a user interface that may be displayed to provide a planning view which displays a graphical representation of generic bone with extracted (e.g., registered) landmarks (shown as bright points), and a graphical representation of what surfaces have been acquired through palpation operations.

The bone palpation operations can be used in many ways acquired and extracted landmarks, and which may vary based on whether the operations are for a computer assisted navigation procedure (e.g., robotic) versus manual navigated procedure, and whether the operations are used with an imageless or CT-based procedure.

For example, in a patient registration workflow for computer assisted navigation procedure or manual navigated procedure with imageless or CT-based images, the bone palpation operations can be used to acquire and extract landmarks.

In a workflow for display bone 3D model for computer assisted navigation procedure: for an imageless process, a generic bone model can have dimensions updated based on acquired and extracted landmarks through bone palpation operations; or for CT-based image process a reconstructed 3D model of the patient anatomy can be generated based on pre-operative CT images and based on acquired and extracted landmarks through bone palpation operations.

In a workflow for display bone 3D model for manual navigated procedure: for an imageless process, a generic bone model may not have dimensions updated based on acquired and extracted landmarks through bone palpation operations; or for CT-based image process a reconstructed 3D model of the patient anatomy can be generated based on pre-operative CT images and may or may not be based on acquired and extracted landmarks through bone palpation operations.

In a workflow for display of navigated instruments together with bone model for computer assisted navigation procedure: for imageless process no navigated instrument may be displayed together with the bone 3D model; or for CT-based image process a navigated saw blade may be displayed together with the bone 3D model.

In a workflow for display bone 3D model for manual navigated procedure, for imageless or CT-based image process a navigation guide may be displayed together with a bone 3D model to guide the user for cut block localization pins insertion.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A system for computer assisted navigation during surgery, comprising at least one processor operative to:
identify a first set of locations of fiducials of a reference element on a ball tip stylus in images obtained from tracking cameras with at least partially overlapping field-of-views imaging the ball tip stylus with a ball palpating a surface of a bone;
determine a first set of locations of a center of the ball based on the first set of locations of the fiducials of the reference element;
define an offset-acquired surface of the bone based on mathematically connecting the first set of locations of the center of the ball;
determine a first set of local normal vectors to the offset-acquired surface for the first set of locations of the center of the ball; and
translate the offset-acquired surface of the bone toward the surface of the bone along the first set of local normal vectors based on a radius of the ball to define an acquired surface of the bone,
the system further comprising:
a camera tracking system including a plurality of spaced cameras;
a tracked reference array adapted to be attached to a bone and configured to be tracked by the cameras;
the ball tip shaped stylus having a plurality of tracking markers configured to be tracked by the cameras and a ball tip shaped to continuously paint a surface of the bone,
wherein the at least one processor is further operative to:
register the acquired surface of the bone in an algorithm for computer assisted navigation during surgery; and
display a graphical representation of the acquired surface of the bone in a planning view for computer assisted navigation during surgery.

2. The system of claim 1, wherein the operation to translate the offset-acquired surface of the bone toward the surface of the bone along the first set of local normal vectors based on the radius of the ball to define the acquired surface of the bone, comprises the at least one processor to:
translate the first set of locations of the center of the ball toward the surface of the bone along the first set of local normal vectors by the radius of the ball to define a first set of locations of the acquired surface of the bone; and mathematically connect the first set of locations of the acquired surface of the bone to define the acquired surface of the bone.

3. The system of claim 1, wherein the operation to define the offset-acquired surface of the bone based on mathematically connecting the first set of locations of the center of the ball, comprises the at least one processor to:
identify among the first set of locations of the center of the ball an outlier location of the center of the ball where the ball is not palpating the surface of the bone; and
define the offset-acquired surface of the bone based on mathematically connecting the first set of locations of the center of the ball without mathematically connecting the outlier location of the center of the ball where the ball is not palpating the surface of the bone.

4. The system of claim 3, wherein the operation to identify among the first set of locations of the center of the ball the outlier location of the center of the ball where the ball is not palpating the surface of the bone, comprises the at least one processor to:
identify the outlier location of the center of the ball where the ball is not palpating the surface of the bone based on the outlier location of the center of the ball having at least a first threshold distance, in a direction along the local normal vector to the offset-acquired surface, from other ones of the first set of locations of the center of the ball which are within a second threshold distance in a direction along the offset-acquired surface of the bone.

5. The system of claim 1, wherein the acquired surface of the bone defines anterior and distal condylar surfaces of a femur palpated by the ball, and the at least one processor is further operative to:
acquire locations of a tibial plateau based on locations of the anterior and distal condylar surfaces of the femur defined by the acquired surface of the bone;
register locations of a tibia in a tracking space based on the acquired locations of the tibial plateau.

6. The system of claim 5, wherein the at least one processor is further operative to, following tibial resection:
identify a second set of locations of the fiducials of the reference element on the ball tip stylus in further images obtained from the tracking cameras imaging the ball tip stylus with the ball palpating a posterior surface of femoral condyles;
determine a second set of locations of the center of the ball based on the second set of locations of the fiducials of the reference element;
define an offset-acquired surface of the posterior surface of femoral condyles based on mathematically connecting the second set of locations of the center of the ball;
determine a second set of local normal vectors to the offset-acquired surface of the posterior surface of the femoral condyles for the second set of locations of the center of the ball; and
translate the offset-acquired surface of the posterior surface of femoral condyles toward the posterior surface of femoral condyles along the second set of local normal vectors based on the radius of the ball to define an acquired surface of the posterior surface of femoral condyles.

7. The system of claim 5, wherein the at least one processor is further operative to:
identify locations of fiducials of a tibial reference element attached to the tibia and locations of fiducials of a femoral reference element attached to the femur in images obtained from the tracking cameras while the ball is palpating the femur; and acquire location a posterior condylar axis based on the registered locations of the tibia and based on the identified locations of the fiducials of the tibial reference element and the femoral reference element.

8. The system of claim 7, wherein the operation to acquire location of the posterior condylar axis based on the registered locations of the tibia and based on the identified locations of the fiducials of the tibial reference element and the femoral reference element, comprises the at least one processor to:

determine a distal femoral plane to be virtually attached to the femur and pass through a posterior surface of femoral condyles;

acquire locations of a tibial plateau based on locations of the anterior and distal surfaces of the femur defined by the acquired surface of the bone and based on the identified locations of the fiducials of the tibial reference element;

determine a proximal tibial plane which is virtually attached to the tibia; and determine a posterior condylar axis based on tracking movement of locations of the fiducials of the tibial reference element relative to locations of the fiducials of the femoral reference element as the tibia is rotated relative to the femur.

9. The system of claim 8, wherein the operation to determine the posterior condylar axis based on tracking movement of locations of the fiducials of the tibial reference element relative to locations of the fiducials of the femoral reference element as the tibia is rotated relative to the femur, comprises the at least one processor to:

determine the posterior condylar axis based on identifying location of intersection of the distal femoral plane and the proximal tibial plane.

10. The system of claim 8, wherein the operation to determine the distal femoral plane comprises the at least one processor to:

determine the distal femoral plane to be normal to a femoral mechanical axis, virtually attached to the femur, and pass through the posterior surface of femoral condyles.

11. The system of claim 1, wherein the at least one processor is further operative to:

acquire location of hip center based on tracking movement of locations of fiducials of a femoral reference element attached to a femur during rotation of the femur;

acquire location of a Whiteside's line based on determining location of the center of the ball palpating a femur surface location corresponding to the Whiteside's line; and register in an algorithm for computer assisted navigation during surgery, the location of hip center and the location of the Whiteside's line.

12. The system of claim 11, wherein the at least one processor is further operative to:

display in a planning view for computer assisted navigation during surgery, the location of hip center and the location of the Whiteside's line.

13. The system of claim 1, wherein the at least one processor is further operative to:

acquire location of a femoral distal mechanical axis point based on determining location of the center of the ball palpating a surface between the femoral condyles;

acquire location of a femoral medial epicondyle based on determining location of the center of the ball palpating a femur surface location corresponding to the femoral medial epicondyle;

acquire location of a femoral lateral epicondyle based on determining location of the center of the ball palpating a femur surface location corresponding to the femoral lateral epicondyle;

acquire location of a femoral medial distal condylar point based on determining a most distal location of an acquired surface of the femoral medial distal condylar palpated by the ball;

acquire location of a femoral lateral distal condylar point based on determining a most distal location of an acquired surface of the femoral lateral distal condylar palpated by the ball;

acquire location of a femoral medial posterior condylar point based on determining a most posterior location of an acquired surface of the femoral medial posterior condylar palpated by the ball;

acquire location of a femoral lateral posterior condylar point based on determining a most posterior location of an acquired surface of the femoral lateral posterior condylar palpated by the ball;

acquire location of a femoral anterior reference surface based on determining locations of an acquired surface of the femoral anterior reference surface palpated by the ball; and register in an algorithm for computer assisted navigation during surgery, the location of the femoral distal mechanical axis point, the location of the femoral medial epicondyle, the location of the femoral lateral epicondyle, the location of the femoral medial distal condylar point, the location of the femoral lateral distal condylar point, the location of the femoral medial posterior condylar point, the location of the femoral lateral posterior condylar point, and the location of the femoral anterior reference surface.

14. The system of claim 13, wherein the at least one processor is further operative to:

display in a planning view for computer assisted navigation during surgery, the location of the femoral distal mechanical axis point, the location of the femoral medial epicondyle, the location of the femoral lateral epicondyle, the location of the femoral medial distal condylar point, the location of the femoral lateral distal condylar point, the location of the femoral medial posterior condylar point, and the location of the femoral lateral posterior condylar point.

15. The system of claim 13, wherein the at least one processor is further operative to:

display in a view for computer assisted navigation during surgery, a graphical representation of the femoral condyles with an indication for a user to acquire the location of the femoral distal mechanical axis point;

display in another view for computer assisted navigation during surgery, a graphical representation of the femoral medial condyles with an indication for the user to acquire the location of the femoral medial epicondyle;

display in another view for computer assisted navigation during surgery, a graphical representation of the femoral lateral condyles with an indication for the user to acquire the location of the femoral lateral epicondyle;

display in another view for computer assisted navigation during surgery, a graphical representation of the femoral condyles with an indication for the user to acquire the location of the femoral medial distal condylar point;

display in another view for computer assisted navigation during surgery, a graphical representation of the femoral condyles with an indication for the user to acquire the location of the femoral lateral distal condylar point;

display in another view for computer assisted navigation during surgery, a graphical representation of the femoral condyles with an indication for the user to acquire the location of the femoral medial posterior condylar point;

display in another view for computer assisted navigation during surgery, a graphical representation of the femoral condyles with an indication for the user to acquire the location of the femoral lateral posterior condylar point; and display in another view for computer assisted navigation during surgery, a graphical representation of the femoral condyles with an indication for the user to acquire the location of the femoral anterior reference surface.

16. The system of claim 1, wherein the at least one processor is further operative to:

acquire location of an ankle medial melleolus point based on determining location of the center of the ball palpating an ankle surface location corresponding to the ankle medial melleolus point;

acquire location of an ankle lateral melleolus point based on determining location of the center of the ball palpating an ankle surface location corresponding to the ankle lateral melleolus point;

acquire location of a tibial proximal mechanical axis point based on determining location of the center of the ball palpating a tibia location corresponding to the tibial proximal mechanical axis point;

acquire location of a tibial anterior reference point based on determining location of the center of the ball palpating a tibia location corresponding to the tibial anterior reference point;

acquire location of a tibial medial plateau point based on determining location of the center of the ball palpating a tibia location corresponding to the tibial medial plateau point;

acquire location of a tibial lateral plateau point based on determining location of the center of the ball palpating a tibia location corresponding to the tibial lateral plateau point;

acquire location of a tibial anterior-posterior line based on determining location of the locations of fiducials of a reference element while the ball tip stylus is oriented corresponding to the tibial anterior-posterior line while the ball is palpating a tibia location corresponding to the tibial anterior-posterior line;

acquire location of a tibial posterior point based on determining location of the center of the ball palpating a tibia location corresponding to the tibial posterior point; and register in an algorithm for computer assisted navigation during surgery, the defined femoral anterior reference surface, the location of the ankle medial melleolus point, the location of the ankle lateral melleolus point, the location of the tibial proximal mechanical axis point, the location of the tibial anterior reference point, the location of the tibial medial plateau point, the location of the tibial lateral plateau point, the location of the tibial anterior-posterior line, and the location of the tibial posterior point.

17. The system of claim 16, wherein the at least one processor is further operative to:

display in a planning view of the algorithm for computer assisted navigation during surgery, the location of the ankle medial melleolus point, the location of the ankle lateral melleolus point, the location of the tibial proximal mechanical axis point, the location of the tibial anterior reference point, the location of the tibial medial plateau point, the location of the tibial lateral plateau point, the location of the tibial anterior-posterior line, and the location of the tibial posterior point.

18. The system of claim 16, wherein the at least one processor is further operative to:

display in a view for computer assisted navigation during surgery, a graphical representation of an ankle with an indication for a user to acquire the location of the ankle medial melleolus point;

display in a view for computer assisted navigation during surgery, a graphical representation of an ankle with an indication for a user to acquire the location of the ankle lateral melleolus point;

display in a view for computer assisted navigation during surgery, a graphical representation of the femoral condyles with an indication for the user to acquire the location of the tibial proximal mechanical axis point;

display in a view for computer assisted navigation during surgery, a graphical representation of the femoral condyles with an indication for the user to acquire the location of the tibial anterior reference point;

display in a view for computer assisted navigation during surgery, a graphical representation of the femoral condyles with an indication for the user to acquire the location of the tibial medial plateau point;

display in a view for computer assisted navigation during surgery, a graphical representation of the femoral condyles with an indication for the user to acquire the location of the tibial lateral plateau point;

display in a view for computer assisted navigation during surgery, a graphical representation of the femoral condyles with an indication for the user to acquire the location of the tibial anterior-posterior line; and display in a view for computer assisted navigation during surgery, a graphical representation of the femoral condyles with an indication for the user to acquire the location of the tibial posterior point.

19. A system for computer assisted navigation during surgery, comprising:

a camera tracking system including a plurality of spaced cameras;

a tracked reference array adapted to be attached to a bone and configured to be tracked by the cameras during the surgery;

a hand held tracked probe having a plurality of tracking markers configured to be tracked by the cameras and a ball tip shaped to continuously paint a surface of the bone during the surgery;

a processor coupled to the camera tracking system and configured to:

identify a first set of locations of the tracking markers of the tracked probe as the ball tip paints across the bone surface;

determine a first set of locations of a center of the ball based on the identified first set of locations of the tracking markers;

determine a 3-dimensional bone surface based on the determined first set of locations of the ball center, wherein the at least one processor is further operative to:

register the acquired surface of the bone in an algorithm for computer assisted navigation during surgery; and display a graphical representation of the acquired surface of the bone in a planning view for computer assisted navigation during surgery.

\* \* \* \* \*